US008822695B2

(12) United States Patent
Buller et al.

(10) Patent No.: US 8,822,695 B2
(45) Date of Patent: Sep. 2, 2014

(54) VIOLET LASER EXCITABLE DYES AND THEIR METHOD OF USE

(71) Applicant: Life Technologies Corporation, Carlsbad, CA (US)

(72) Inventors: Gayle Buller, Springfield, OR (US); Jixiang Liu, Eugene, OR (US); Stephen Yue, Eugene, OR (US); Jolene Bradford, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 13/777,910

(22) Filed: Feb. 26, 2013

(65) Prior Publication Data

US 2013/0273569 A1    Oct. 17, 2013

Related U.S. Application Data

(63) Continuation of application No. 13/149,392, filed on May 31, 2011, now Pat. No. 8,415,477, which is a continuation of application No. 11/535,458, filed on Sep. 26, 2006, now Pat. No. 8,158,801.

(60) Provisional application No. 60/745,599, filed on Apr. 25, 2006, provisional application No. 60/720,690, filed on Sep. 26, 2005.

(51) Int. Cl.
C07D 409/04 (2006.01)
G01N 33/52 (2006.01)

(52) U.S. Cl.
USPC ........................ 546/280.4; 436/546

(58) Field of Classification Search
USPC .................. 546/280.4; 436/546; 435/4
See application file for complete search history.

(56) References Cited

U.S. PATENT DOCUMENTS

| 3,996,345 A | 12/1976 | Ullman et al. |
| 4,374,120 A | 2/1983 | Soini |
| 4,506,368 A | 3/1985 | Lee |
| 4,542,104 A | 9/1985 | Stryer et al. |
| 4,603,422 A | 7/1986 | Fletcher |
| 4,711,955 A | 12/1987 | Ward et al. |
| 5,047,519 A | 9/1991 | Hobbs et al. |
| 5,252,191 A | 10/1993 | Pauli et al. |
| 5,352,803 A | 10/1994 | Mattingly |
| 5,362,628 A | 11/1994 | Haugland et al. |
| 5,573,904 A | 11/1996 | Mattingly |
| 5,714,327 A | 2/1998 | Houthoff et al. |
| 6,306,628 B1 | 10/2001 | Rothschild et al. |
| 2003/0212455 A1 | 11/2003 | Steensel et al. |
| 2007/0077549 A1 | 4/2007 | Buller et al. |

FOREIGN PATENT DOCUMENTS

| GB | 00900815 | 7/1962 |
| JP | S49-046622 | 9/1972 |
| JP | HEI04-503212 | 7/1992 |
| JP | HEI04-225951 | 8/1992 |
| JP | 05/071538 | 3/2005 |
| WO | 90/09381 | 8/1990 |
| WO | 01/20331 | 3/2001 |
| WO | 01/68807 | 9/2001 |
| WO | 2005/020982 | 3/2005 |
| WO | 2007/038659 | 4/2007 |

OTHER PUBLICATIONS 06815641.3, "Extended European Search Report mailed on Mar. 19, 2010".
06815641.3, "Office Action mailed May 9, 2011".
06815641.3, "Response to Jul. 7, 2010 Office Action mailed", Filed on Jan. 17, 2011.
068156413, "Office Action Mailed Jul. 7, 2010".
U.S. Appl. No. 11/535,458, "Non-Final office action mailed on Aug. 30, 2010", 12 pages.
U.S. Appl. No. 11/535,458, "Notice of Allowance mailed on Mar. 8, 2011", 11 pages.
U.S. Appl. No. 11/535,458, "Office Action mailed Feb. 5, 2010", 6 pages.
U.S. Appl. No. 11/535,458, "Office Action Mailed Aug. 20, 2009", 6 pages.
U.S. Appl. No. 11/535,458, "Response to Non-Final Office Action dated Aug. 30, 2010 filed Jan. 31, 2011".
U.S. Appl. No. 11/535,458, "Response to Office Action dated Feb. 5, 2010 filed Jul. 30, 2010".
U.S. Appl. No. 11/535,458, "Response to Office Action dated Aug. 20, 2009 filed Nov. 18, 2009".
Al-Azawe, S. S., "Synthesis of 2,5-di su bstituted thiazoles and their reactions with grignard reagents", *J. Iraq i Chem. Soc.*; vol. 13, 1988, pp. 1-13.
Berge, Stephen M. et al., "Pharmaceutical Salts" *Journal of Pharmaceutical Science*, vol. 66, 1977, pp. 1-19.
Brinkley, Michael, "A Brief Survey of Methods for Preparing Protein Conjugates with Dyes, Haptens, and Cross-Linking Reagents", *Bioconjugate Chemistry*, vol. 3, Issue 1, 1992, pp. 2-13.
Fletcher, A. N. et al., "Fluorescence and lasing Characteristics of some long-lived flashlamp-pumpable Oxazole Dyes", *Optics Comm.*; vol. 48(5), 1984, pp. 352-356.
Furniss, Brian S. et al., "Resolution of Racemates" *Vogel's Textbook of Practical Organic Chemistry*, Fifth Ed, Longman Group UK Ltd., Essex, 1989, pp. 809-823.
Gorevic, Peter D. et al., "Immunoglobulin G (IgG)", *Methods in Enzymology*, vol. 116, 1985, pp. 3-25.
Haugland, Richard P. , "Molecular Probes Handbook of Fluorescent Probes and Research Products", *Ninth Edition, CD ROM, Table of Contents*, Molecular Probes, Inc., 2002, pp. 1-6.

(Continued)

*Primary Examiner* — Charanjit Aulakh
(74) *Attorney, Agent, or Firm* — Life Technologies Corporation

(57) ABSTRACT

The present invention provides dye compounds optimally excited at about 400 nm and have a Stokes shift of at least about 80 nm. These dyes find use in detection of analyte in a sample and the preparation of dye-conjugates.

16 Claims, 10 Drawing Sheets

(56) References Cited

OTHER PUBLICATIONS

Hedelberg, John F. et al., "The genome sequence of *Vibrio cholerae*, the etiologic agent of cholera.", *Nature*, vol. 406, Aug. 3, 2000, pp. 477-483.

Helgason, Erlendur et al., "*Bacillus anthracis, Bacillus cereus*, and *Bacillus thuringiensis*—One Species on the Basis of Genetic Evidence.", *Appl. Envir. Microbiol.*, vol. 66, 2000, pp. 2627-2630.

Heller, A., "Electrical Wiring of Redox Enzymes", *Acc. Chem. Res.*, vol. 23, No. 5, 1990, pp. 128-134.

Hemmila, Ilkka, "Fluoroimmunoassays and immunofluorometric assays", *Clin. Chem.*, vol. 31, 1985, 359.

Jiang, Sunny C. et al., "Genetic diversity of clinical and environmental isolates of *Vibrio cholerae* determined by amplified fragment length polymorphism (AFLP).", *Appl. Envir. Microbiol.*, 66, 2000, pp. 148-153.

Jolley, Michael E. et al., "Flourescence polarization immunoassay I. Monitoring aminoglycosides antibiotics in serum and plasma.", *Clin. Chem.*, vol. 27, 1981, pp. 1190-1197.

Kanaoka, Yuichi, "Organic fluorescence. reagents in the study of enzymes and proteins.", *Angewandte Chemie International Edition*, vol. 16, 1977, pp. 137-147.

Kauffman, J. M. et al., "Syn thes is and photophysical properties of some 5 (2 )-aryl-2 (5 )-(4-pyridyl)oxazoles and related oxad iazoles and furans", *J. Heterocyc. Chern.*; vol. 29, 1992, pp. 1245-1273.

Kovach, N. A. et al., "Aromatic electrolytes: interionic association of 4,4'-dipridylium salts", *Zhurnal Organicheskoi Khimii*, 32(4), 1996, pp. 625-628.

Kubin, R. F. et al., "Anionic and Zwittrionic Photophysical Effects in Some Pyridinum Oxazole Laser Dyes", *Laser Chemistry*, vol. 10, No. 4, 1990, pp. 247-258.

Li, Zhongjie et al., "Synthesis and Spectroscopic Properties of 10, 10-dimethyl-6-phenyl-8-(5-substituted-2-furfuryl)-10H-pyrido[1,2-a]indolium salts", *Kexue Tongbao*, 33(11),, 1988, pp. 912-915.

Litak, P. T. et al., "Sytheneses of Reactive Fluorescent Stains Derived from 5(2)-aryl-2(5)-(4-pyridy) Oxazoles and Bifunctionally Reactive Linkers", *Journal of Heterocyclic Chemistry*, vol. 31, No. 2, 1994, pp. 457-479.

PCT/US2006/037794 *PCT Written Opinion*, Feb. 21, 2007.

PCT/US2006/037794 *PCT International Search Report*, Feb. 21, 2007, pp. 1-3.

PCT/US2006/037794, "International Preliminary Report on Patentability", Mar. 26, 2008, pp. 1-6.

Salafsky, J. S., ""SHG-Label" for Detection of Molecules by Second Harmonic Generation", *Chemical Physics Letters*, vol. 342, No. 5, 6, 2001, pp. 485-491.

Sandler, Stanley R. et al., "Organic Functional Group Preparations", vol. 3, *New York: Academic Press*, 1972, pp. 5-7.

Sezen, B. et al., "Diversity Synthesis via C—H Bond Functionalization: Concept-guided Development of new C-Arylation Methods for Imidazoles", *J.Am.Chem.Soc.*; vol. 125(35), 2003, pp. 10580-10585.

Shimizu, K. et al., "A novel fluorescent Silica Tracer for biological Silification Studies", *Chemistry & Biology*; vol. 8, 2001, pp. 1051-1060.

Spatola, et al., "Ch 5: Peptide Backbone Modifications: A Structure—Activity Analysis of Peptides Containing Amide Bond Surrogates, Conformational Constraints, and Rela", *Chemistry Biochemistry of Amino Acids, Peptides and Proteins*, vol. 7, 1983, pp. 267-357.

Volchkov, V. V. et al., "Acid-Base Interaction of Pyridyl(naphthyl)oxadiazoles with sulfuric Aci din the Ground and Exi ted States", *Russ.J.Gen.Chem.*; vol. 68(1), 1998, pp. 142-144.

Wang, Q. et al., "Phosphorylation-driven Protein-Protein Interactions: A Protein Kinase Sensing System", *J.Am.Chem.Soc.*; vol. 127(21), 2005, pp. 7684-7685.

US 8,822,695 B2

VIOLET LASER EXCITABLE DYES AND THEIR METHOD OF USE

CROSS-REFERENCE TO RELATED APPLICATIONS

This application claims priority to U.S. Ser. No. 60/720,690, filed Sep. 26, 2005; and U.S. Ser. No. 60/745,599 filed Apr. 25, 2006, which disclosures are herein incorporated by reference.

INTRODUCTION

1. Field of the Invention

The invention relates to colored and fluorescent dyes, including reactive dye derivatives, and dye-conjugates; and to their use in staining samples and detecting ligands or other analytes. The invention has applications in the fields of cell biology, neurology, immunology, pathology and proteomics.

2. Background of the Invention

Fluorescent dyes are widely used as tracers for localization of biological structures by fluorescence microscopy, for quantification of analytes by fluorescence immunoassay, for flow cytometric analysis of cells, for measurement of physiological state of cells and other applications (Kanaoka, Angew. *Chem. Intl. Ed. Engl.* 16: 137 (1977); Hemmila, *Clin. Chem.* 31: 359 (1985)). Among the advantages of fluorescent agent over other types of absorption dyes include the detectability of emission at a wavelength distinct from the excitation, the orders of magnitude greater detectability of fluorescence emission over light absorption, the generally low level of fluorescence background in most biological samples and the measurable intrinsic spectral properties of fluorescence polarization (Jolley et al., *Clin. Chem.* 27: 1190 (1981)), lifetime (U.S. Pat. No. 4,374,120) and excited state energy transfer (U.S. Pat. Nos. 3,996,345; and 4,542,104).

Fluorescent agents are now widely used to determine physiological functions in patients during routine checkups or diagnostic procedures, to monitor the exposure of workers and others to potentially harmful chemicals such as toxic or carcinogenic pesticides or inorganic materials in the atmosphere, soil, or drinking water, in determining the effectiveness of pharmaceuticals on disease states or conditions, in screening new compounds for biological activity as either promoters or inhibitors of particular enzymes, in monitoring gene and transgene expression, and in performing immunological and other laboratory assays such as enzyme-linked immunosorbent assays (ELISAs) and Western blots.

Optical methods of detection, such as fluorescence emission, UV absorptivity, and colorimetry are convenient and highly effective for detecting, monitoring, and measuring fluorescent agents, since methods such as these can generate either qualitative or quantitative information and detection can be achieved either by direct visual observation or by instrumentation.

For many applications that utilize fluorescent dyes as tracers, it is necessary to chemically react the dye with a biologically active ligand such as a cell, tissue, protein, antibody, enzyme, drug, hormone, nucleotide, nucleic acid, polysaccharide, lipid or other biomolecule to make a fluorescent ligand analog or to react the dye with natural or synthetic polymers. With these synthetic probes, the biomolecule frequently confers a specificity for a biochemical interaction that is under investigation and the fluorescent dye provides the method for detection and/or quantification of the interaction. Thus, useful dyes are based on a versatile fluorescent nucleus that allows the preparation of reactive derivatives of several different types that exhibit reactivity toward a variety of chemically reactive sites.

There is a recognized need for suitable fluorophores, particularly reactive fluorophores, for applications in multi-color, multiplexed applications, such as microscopy, flow cytometry, immunoassays, and nucleic acid sequencing. Presently there exists a need for a dye that is excited by a violet 405 nm laser, which is not excited by the 488 nm argon laser, with a long Stokes shift allowing for use of multiple lasers.

The existing, violet laser excitable dyes, about 405 nm, generally have a weak absorbtivity (extinction coefficients of less than 20,000 cm$^{-1}$ M$^{-1}$ at their absorbance maxima), relatively low quantum yields, and/or or not particularly well solubilized in aqueous environments. Such properties are less than ideal for a fluorophore of interest for biological applications. Cascade Yellow is a common violet laser excitable dye, however this dye is relatively dim when conjugated to a carrier molecule or solid support and has a tendency to aggregate in an aqueous solution.

For example, the wide emission band-widths of many art-recognized dyes result in significant residual fluorescence background from the violet excited dyes at wavelengths typically used for detection of fluorescein emission (typically 515 to 525 nm). Moreover, fluorescence of many of the art-recognized dyes is frequently quenched in aqueous solution, resulting in low quantum yields. The lower quantum yield decreases the detection sensitivity or requires use of disproportionately larger quantities of the less fluorescent dye.

In view of the above, a fluorophore having a reactive group attached to the fluorescent nucleus of the fluorophore, which is water soluble, and highly fluorescent within a narrow wavelength range would be a highly desirable addition to the art-recognized array of reactive fluorophores. The present invention provides such fluorescent agents, conjugates incorporating the agents and methods of using the agents and their conjugates.

SUMMARY OF THE INVENTION

Provided are compounds having the structure

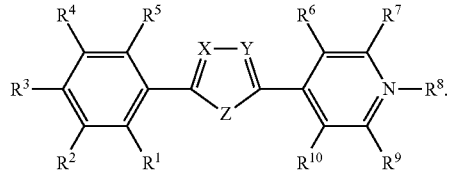

X, Y and Z are independently carbon, —CR$^{12}$, nitrogen, —NR$^{14}$, sulfur, oxygen, selenium, phosphorous, silicon, arsenic, amido, C—C, CR$^{12}$-CR$^{13}$, NR$^{14}$—NR$^{15}$, or S—S, wherein at least one of X, Y and Z is other than carbon or C—C.

R$^{12}$-R$^{15}$ are independently hydrogen, alkyl, substituted alkyl, alkoxy, hydroxy, sulfo, halogen, amino, substituted amino, aldehyde, carboxylic acid, ester, azido, nitro, nitroso, cyano, or thioether.

R$^1$-R$^7$ and R$^9$-R$^{10}$ are independently is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7 aromatic or heteroaromatic ring or R$^1$-R$^7$ and R$^9$-R$^{10}$ comprises a reactive group, carrier molecule or solid support. $R^8$ is hydrogen, alkyl, substituted alkyl, 5-, 6- or 7-aromatic or heteroaromatic ring, substituted 5-, 6- or 7-aromatic or heteroaromatic ring or $R^8$ comprises a reactive group, carrier molecule or solid support. Alternatively, a member selected from $R^1$ in combination with $R^2$;
$R^2$ in combination with $R^3$;
$R^3$ in combination with $R^4$;
$R^4$ in combination with $R^5$;
$R^6$ in combination with $R^7$;
$R^7$ in combination with $R^8$;
$R^8$ in combination with $R^9$; and
$R^9$ in combination with $R^{10}$;

together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl.

In one embodiment these compounds are excited from about 350 nm to about 500 nm, more preferably these compounds are excited with a wavelength from about 380 nm to about 420 nm. Particularly preferred are compounds 9A, 9B, 9C and 31.

Also provided are both methods for forming a dye conjugate and methods for detecting an analyte in a sample. The method for detecting an analyte in sample comprises: combining a present compound with a sample to form a combined sample; incubating the combined sample for a sufficient amount of time for the compound to associate with the analyte in the sample to form an incubated sample; illuminating the incubated sample with an appropriate wavelength to form an illuminated sample; and detecting the illuminated sample whereby the analyte in the sample is detected.

The method for forming a dye conjugate comprises the steps of: combining a present compound with a carrier molecule or solid support to form a combined sample, wherein the compound comprises a reactive group; and incubating the combined sample for a sufficient amount of time for the compound to form a covalent bond with either the carrier molecule or solid support.

Further provided are kits for detecting an analyte in a sample and kits for forming a dye conjugate according to the disclosed methods. The kits typically comprises a present compound and instructions for forming a dye conjugate and/or detecting an analyte in a sample.

DETAILED DESCRIPTION OF THE INVENTION

Introduction

Figure 1:
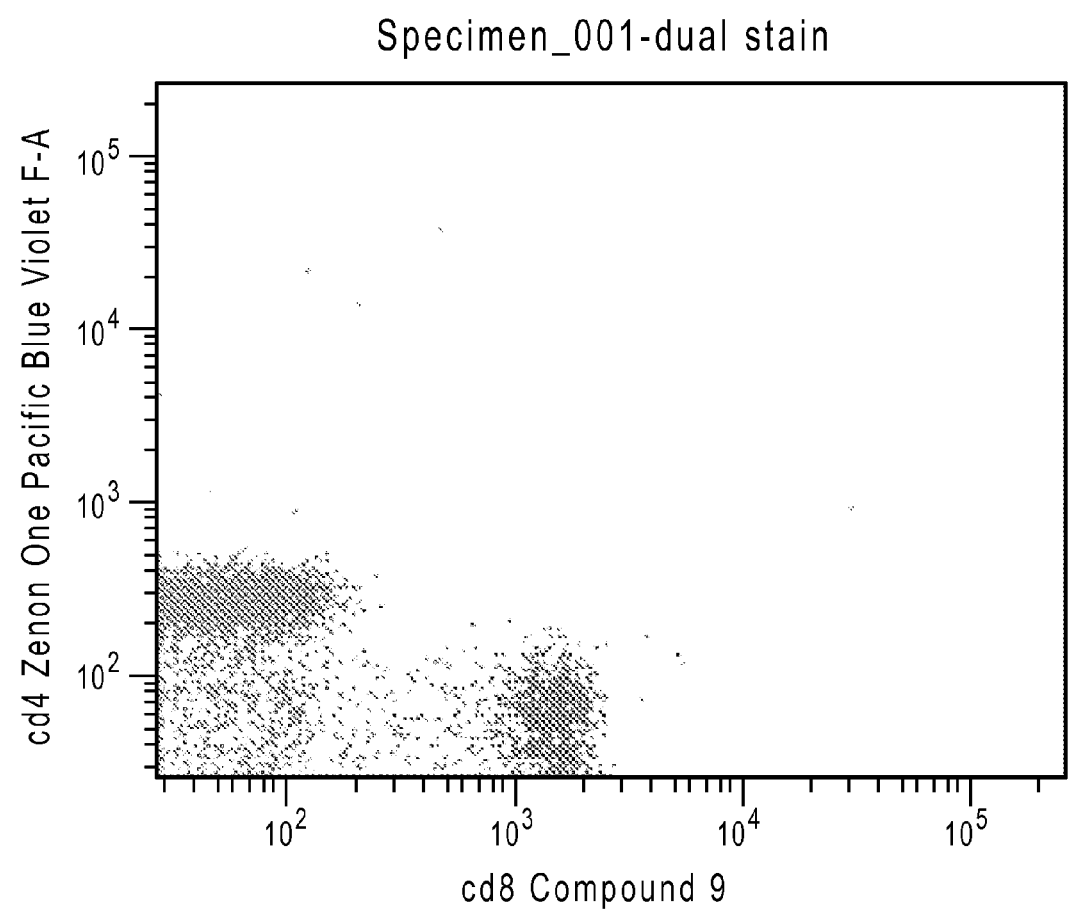
FIG. 1: Shows the immunophenotyping using Pacific Blue Dye and Compound 9.
Figure 2:
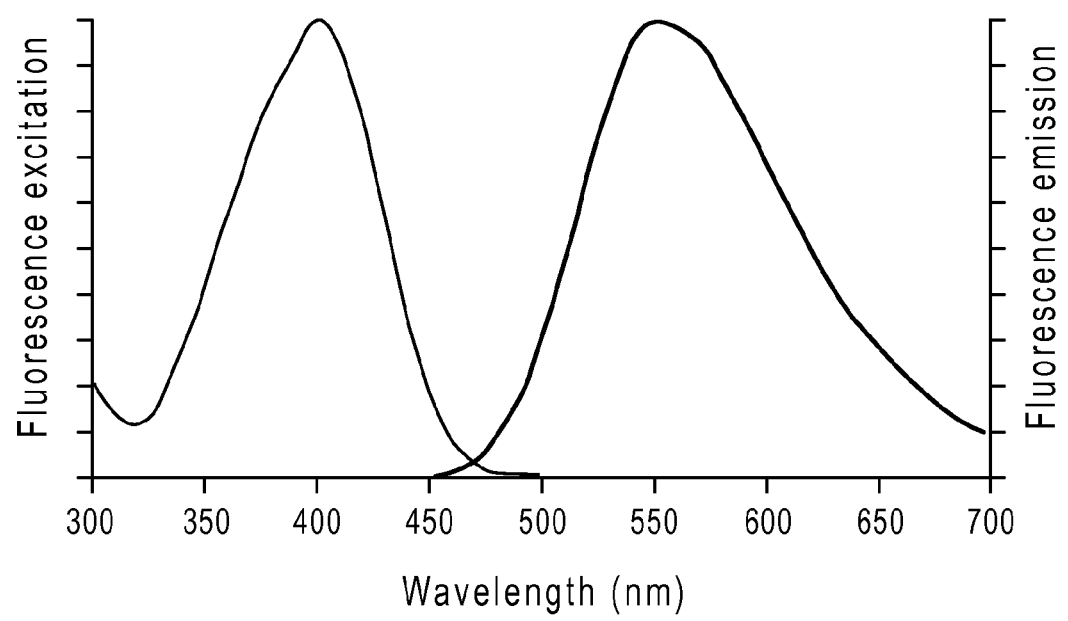
FIG. 2: Shows the excitation and emission spectra of Compound 9A.

There is a continuous and expanding need for rapid, highly specific methods of detecting and quantifying chemical, biochemical and biological analytes in research and diagnostic mixtures. Of particular value are methods for measuring small quantities of nucleic acids, peptides (e.g., enzymes), pharmaceuticals, metabolites, microorganisms and other materials of diagnostic value. Examples of such materials include narcotics and poisons, drugs administered for therapeutic purposes, hormones, pathogenic microorganisms and viruses, antibodies, and enzymes and nucleic acids, particularly those implicated in disease states.

The present invention provides dye compounds that have an absorption of about 350 nm to about 500 nm and that have a large Stokes shift, making them ideal for multiplexing experiments and in certain circumstances useful with increasingly popular violet lasers. The compounds are based on the Cascade Yellow fluorophore. Analogs of the Cascade Yelloe dye showed surprising and unexpected results with regard to brightness of signal, stability, water solubility and the apparently total loss of quenching with a high DOS.

Definitions

Before describing the present invention in detail, it is to be understood that this invention is not limited to specific compositions or process steps, as such may vary. It must be noted that, as used in this specification and the appended claims, the singular form "a", "an" and "the" include plural referents unless the context clearly dictates otherwise. Thus, for example, reference to "a compound" includes a plurality of compounds and reference to "a conjugate" includes a plurality of conjugates and the like.

Unless defined otherwise, all technical and scientific terms used herein have the same meaning as commonly understood by one of ordinary skill in the art to which this invention is related. The following terms are defined for purposes of the invention as described herein.

The symbol ∿∿ , whether utilized as a bond or displayed perpendicular to a bond indicates the point at which the displayed moiety is attached to the remainder of the molecule, solid support, etc.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Certain compounds of the present invention possess asymmetric carbon atoms (optical centers) or double bonds; the racemates, diastereomers, geometric isomers and individual isomers are encompassed within the scope of the present invention.

The compounds of the invention may be prepared as a single isomer (e.g., enantiomer, cis-trans, positional, diastereomer) or as a mixture of isomers. In a preferred embodiment, the compounds are prepared as substantially a single isomer. Methods of preparing substantially isomerically pure compounds are known in the art. For example, enantiomerically enriched mixtures and pure enantiomeric compounds can be prepared by using synthetic intermediates that are enantiomerically pure in combination with reactions that either leave the stereochemistry at a chiral center unchanged or result in its complete inversion. Alternatively, the final product or intermediates along the synthetic route can be resolved into a single stereoisomer. Techniques for inverting or leaving unchanged a particular stereocenter, and those for resolving mixtures of stereoisomers are well known in the art and it is well within the ability of one of skill in the art to choose and appropriate method for a particular situation. See, generally, Furniss et al. (eds.), *Vogel's Encyclopedia of Practical Organic Chemistry*, 5th ed., Longman Scientific and Technical Ltd., Essex, 1991, pp. 809-816; and Heller, *Acc. Chem. Res.* 23: 128 (1990).

The compounds of the present invention may also contain unnatural proportions of atomic isotopes at one or more of the atoms that constitute such compounds. For example, the compounds may be radiolabeled with radioactive isotopes, such as, for example, tritium ($^3H$), iodine-125 ($^{125}I$) or carbon-14 ($^{14}C$). All isotopic variations of the compounds of the present invention, whether radioactive or not, are intended to be encompassed within the scope of the present invention.

Where substituent groups are specified by their conventional chemical formulae, written from left to right, they equally encompass the chemically identical substituents, which would result from writing the structure from right to left, e.g., $-CH_2O-$ is intended to also recite $-OCH_2-$.

"Su" refers to succinimide, succinimidyl or succinimidyl ester.

The term "acyl" or "alkanoyl" by itself or in combination with another term, means, unless otherwise stated, a stable straight or branched chain, or cyclic hydrocarbon radical, or combinations thereof, consisting of the stated number of carbon atoms and an acyl radical on at least one terminus of the alkane radical. The "acyl radical" is the group derived from a carboxylic acid by removing the —OH moiety therefrom.

The term "alkyl," by itself or as part of another substituent means, unless otherwise stated, a straight or branched chain, or cyclic hydrocarbon radical, or combination thereof, which may be fully saturated, mono- or polyunsaturated and can include divalent ("alkylene") and multivalent radicals, having the number of carbon atoms designated (i.e. $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4pentadienyl), ethynyl, 1- and 3-propynyl, 3-butynyl, and the higher homologs and isomers. The term "alkyl," unless otherwise noted, is also meant to include those derivatives of alkyl defined in more detail below, such as "heteroalkyl." Alkyl groups that are limited to hydrocarbon groups are termed "homoalkyl".

Exemplary alkyl groups of use in the present invention contain between about one and about twenty five carbon atoms (e.g. methyl, ethyl and the like). Straight, branched or cyclic hydrocarbon chains having eight or fewer carbon atoms will also be referred to herein as "lower alkyl". In addition, the term "alkyl" as used herein further includes one or more substitutions at one or more carbon atoms of the hydrocarbon chain fragment.

The terms "alkoxy," "alkylamino" and "alkylthio" (or thioalkoxy) are used in their conventional sense, and refer to those alkyl groups attached to the remainder of the molecule via an oxygen atom, an amino group, or a sulfur atom, respectively.

The term "heteroalkyl," by itself or in combination with another term, means, unless otherwise stated, a straight or branched chain, or cyclic carbon-containing radical, or combinations thereof, consisting of the stated number of carbon atoms and at least one heteroatom which is a member selected from the group consisting of O, N, Si, P and S, and wherein the nitrogen, phosphorous and sulfur atoms are optionally oxidized, and the nitrogen heteroatom is optionally be quaternized. The heteroatom(s) O, N, P, S and Si may be placed at any interior position of the heteroalkyl group or at the position at which the alkyl group is attached to the remainder of the molecule. Examples include, but are not limited to, $-CH_2-CH_2-O-CH_3$, $-CH_2-CH_2-NH-CH_3$, $-CH_2-CH_2-N(CH_3)-CH_3$, $-CH_2-S-CH_2-CH_3$, $-CH_2-CH_2$, $-S(O)-CH_3$, $-CH_2-CH_2-S(O)_2-CH_3$, $-CH=CH-O-CH_3$, $-Si(CH_3)_3$, $-CH_2-CH=N-OCH_3$, and $-CH=CH-N(CH_3)-CH_3$. Up to two heteroatoms may be consecutive, such as, for example, $CH_2-NH-OCH_3$ and $-CH_2-O-Si(CH_3)_3$. Similarly, the term "heteroalkylene" by itself or as part of another substituent means a divalent radical derived from heteroalkyl, as exemplified, but not limited by, $-CH_2-CH_2-S-CH_2-CH_2$ and $-CH_2-S-CH_2-CH_2-NH-CH_2-$. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula $-C(O)_2R'-$ represents both $-C(O)_2R'-$ and $-R'C(O)_2-$.

The terms "cycloalkyl" and "heterocycloalkyl", by themselves or in combination with other terms, represent, unless otherwise stated, cyclic versions of "alkyl" and "heteroalkyl", respectively. Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The term "aryl" means, unless otherwise stated, a polyunsaturated, aromatic moiety that can be a single ring or multiple rings (preferably from 1 to 3 rings), which are fused together or linked covalently. The term "heteroaryl" refers to aryl groups (or rings) that contain from one to four heteroatoms which are members selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, tetrazolyl, benzo[b]furanyl, benzo[b]thienyl, 2,3-dihydrobenzo[1,4]dioxin-6-yl, benzo[1,3]dioxol-5-yl and 6-quinolyl. Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) are generically referred to as "alkyl group substituents," and they can be one or more of a variety of groups selected from, but not limited to: —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R'" and R"" each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R'" and R"" groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

Similar to the substituents described for the alkyl radical, substituents for the aryl and heteroaryl groups are generically referred to as "aryl group substituents." The substituents are selected from, for example: halogen, —OR', =O, =NR', =N—OR', —NR'R", —SR', -halogen, —SiR'R"R'", —OC(O)R', —C(O)R', —CO$_2$R', —CONR'R", —OC(O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S(O)$_2$R', —S(O)$_2$NR'R", —NRSO$_2$R', —CN and —NO$_2$, —R', —N$_3$, —CH(Ph)$_2$, fluoro(C$_1$-C$_4$)alkoxy, and fluoro(C$_1$-C$_4$)alkyl, in a number ranging from zero to the total number of open valences on the aromatic ring system; and where R', R", R'" and R"" are preferably independently selected from hydrogen, substituted or unsubstituted alkyl, substituted or unsubstituted heteroalkyl, substituted or unsubstituted aryl and substituted or unsubstituted heteroaryl. When a compound of the invention includes more than one R group, for example, each of the R groups is independently selected as are each R', R", R'" and R"" groups when more than one of these groups is present. In the schemes that follow, the symbol X represents "R" as described above.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X—(CR"R'")$_d$—, where s and d are independently integers of from 0 to 3, and X is —O—, —NR'—, —S—, —S(O)—, —S(O)$_2$—, or —S(O)$_2$NR'—. The substituents R, R', R" and R'" are preferably independently selected from hydrogen or substituted or unsubstituted (C$_1$-C$_6$)alkyl.

As used herein, the term "heteroatom" includes oxygen (O), nitrogen (N), sulfur (S), phosphorus (P) and silicon (Si).

The term "amino" or "amine group" refers to the group —NR'R" (or N$^+$RR'R") where R, R' and R" are independently selected from the group consisting of hydrogen, alkyl, substituted alkyl, aryl, substituted aryl, aryl alkyl, substituted aryl alkyl, heteroaryl, and substituted heteroaryl. A substituted amine being an amine group wherein R' or R" is other than hydrogen. In a primary amino group, both R' and R" are hydrogen, whereas in a secondary amino group, either, but not both, R' or R" is hydrogen. In addition, the terms "amine" and "amino" can include protonated and quaternized versions of nitrogen, comprising the group —N$^+$RR'R" and its biologically compatible anionic counterions.

The term "aqueous solution" as used herein refers to a solution that is predominantly water and retains the solution characteristics of water. Where the aqueous solution contains solvents in addition to water, water is typically the predominant solvent.

The term "detectable response" as used herein refers to an occurrence of or a change in, a signal that is directly or indirectly detectable either by observation or by instrumentation. Typically, the detectable response is an optical response resulting in a change in the wavelength distribution patterns or intensity of absorbance or fluorescence or a change in light scatter, fluorescence lifetime, fluorescence polarization, or a combination of the above parameters.

The term "dye" as used herein refers to a compound that emits light to produce an observable detectable signal. "Dye" includes fluorescent and nonfluorescent compounds that include without limitations pigments, fluorophores, chemiluminescent compounds, luminescent compounds and chromophores. The term "fluorophore" as used herein refers to a compound that is inherently fluorescent or demonstrates a change in fluorescence upon binding to a biological compound or metal ion, i.e., fluorogenic. Numerous fluorophores are known to those skilled in the art and include, but are not limited to, coumarin, acridine, furan, indole, quinoline, cyanine, benzofuran, quinazolinone, benzazole, borapolyazaindacene and xanthenes, with the latter including fluoroscein, rhodamine, rhodol, rosamine and derivatives thereof as well as other fluorophores described in RICHARD P. HAUGLAND, MOLECULAR PROBES HANDBOOK OF FLUORESCENT PROBES AND RESEARCH CHEMICALS (9$^{th}$ edition, CD-ROM, 2002).

The term "carrier molecule" as used herein refers to a biological or a non-biological component that is covalently bonded to compound of the present invention. Such components include, but are not limited to, an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof.

The term "Linker" or "L", as used herein, refers to a single covalent bond or a series of stable covalent bonds incorporating 1-20 nonhydrogen atoms selected from the group consisting of C, N, O, S and P that covalently attach the fluorogenic or fluorescent compounds to another moiety such as a chemically reactive group or a biological and non-biological component. Exemplary linking members include a moiety that includes —C(O)NH—, —C(O)O—, —NH—, —S—, —O—, and the like. The linker can be used to attach the compound to another component of a conjugate, such as a targeting moiety (e.g., antibody, ligand, non-covalent protein-binding group, etc.), an analyte, a biomolecule, a drug and the like.

The term "peptide", as used herein, refers to a polymer in which the monomers are amino acids and are joined together through amide bonds, alternatively referred to as a polypeptide or a protein. When the amino acids are α-amino acids, either the L-optical isomer or the D-optical isomer can be used. Additionally, unnatural amino acids, for example, β-alanine, phenylglycine and homoarginine are also included. Commonly encountered amino acids that are not gene-encoded may also be used in the present invention. All of the amino acids used in the present invention may be either the D- or L-isomer. The L-isomers are generally preferred. In addition, other peptidomimetics are also useful in the present invention. For a general review, see Spatola, A. F., in *Chemistry and Biochemistry of Amino Acids. Peptides and Proteins*, B. Weinstein, eds., Marcel Dekker, New York, p. 267 (1983).

The term "reactive group" as used herein refers to a group that is capable of reacting with another chemical group to form a covalent bond, i.e. is covalently reactive under suitable reaction conditions, and generally represents a point of attachment for another substance. The reactive group is a moiety, such as carboxylic acid or succinimidyl ester, on the compounds of the present invention that is capable of chemically reacting with a functional group on a different compound to form a covalent linkage. Reactive groups generally include nucleophiles, electrophiles and photoactivatable groups.

Exemplary reactive groups include, but not limited to, olefins, acetylenes, alcohols, phenols, ethers, oxides, halides, aldehydes, ketones, carboxylic acids, esters, amides, cyanates, isocyanates, thiocyanates, isothiocyanates, amines, hydrazines, hydrazones, hydrazides, diazo, diazonium, nitro, nitriles, mercaptans, sulfides, disulfides, sulfoxides, sulfones, sulfonic acids, sulfinic acids, acetals, ketals, anhydrides, sulfates, sulfenic acids isonitriles, amidines, imides, imidates, nitrones, hydroxylamines, oximes, hydroxamic acids thiohydroxamic acids, allenes, ortho esters, sulfites, enamines, ynamines, ureas, pseudoureas, semicarbazides, carbodiimides, carbamates, imines, azides, azo compounds, azoxy compounds, and nitroso compounds. Reactive functional groups also include those used to prepare bioconjugates, e.g., N-hydroxysuccinimide esters, maleimides and the like. Methods to prepare each of these functional groups are well known in the art and their application to or modification for a particular purpose is within the ability of one of skill in the art (see, for example, Sandler and Karo, eds., *Organic Functional Group Preparations*, Academic Press, San Diego, 1989).

The term "salt thereof," as used herein includes salts of the agents of the invention and their conjugates, which are preferably prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of base addition salts include sodium, potassium, calcium, ammonium, organic amino, or magnesium, or a similar salt. When compounds of the present invention contain relatively basic functionalities, acid addition salts can be obtained by contacting the neutral form of such compounds with a sufficient amount of the desired acid, either neat or in a suitable inert solvent. Examples of addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science*, 1977, 66, 1-19). Certain specific compounds of the present invention contain both basic and acidic functionalities that allow the compounds to be converted into either base or acid addition salts.

The term "sample" as used herein refers to any material that may contain an analyte for detection or quantification. The analyte may include a reactive group, e.g., a group through which a compound of the invention can be conjugated to the analyte. The sample may also include diluents, buffers, detergents, and contaminating species, debris and the like that are found mixed with the target. Illustrative examples include urine, sera, blood plasma, total blood, saliva, tear fluid, cerebrospinal fluid, secretory fluids from nipples and the like. Also included are solid, gel or sol substances such as mucus, body tissues, cells and the like suspended or dissolved in liquid materials such as buffers, extractants, solvents and the like. Typically, the sample is a live cell, a biological fluid that comprises endogenous host cell proteins, nucleic acid polymers, nucleotides, oligonucleotides, peptides and buffer solutions. The sample may be in an aqueous solution, a viable cell culture or immobilized on a solid or semi solid surface such as a polyacrylamide gel, membrane blot or on a microarray.

The Compounds

In general, for ease of understanding the present invention, the dye compounds and corresponding substituents will first be described in detail, followed by the many and varied methods in which the compounds find uses, which is followed by exemplified methods of use and synthesis of certain novel compounds that are particularly advantageous for use with the methods of the present invention.

The present compounds are derivatives of the well known fluorophore, Cascade Yellow. Unexpectedly we found that by modifying the core structure we were able to increase the DOL on dye conjugates without significant quenching, resulting, in part, in a brighter signal. In addition, these compounds demonstrated good water solubility, stability and a large Stokes shift.

Cascade Yellow has the following structure:

We found that by modifying the substituent directly attached to the nitrogen, resulted in surprising desirable compounds. Thus, without wishing to be bound by a theory, it appears that this modification directly results in the improved characteristics observed with the present compounds.

The compounds of the invention have the following structure:

wherein

X is independently carbon, —$CR^{12}$, nitrogen, —$NR^{14}$, sulfur, oxygen, selenium, phosphorous, silicon, arsenic, amido, C═C, $CR^{12}$-$CR^{13}$, $NR^{14}$-$NR^{15}$, or S—S;

Y is independently carbon, —$CR^{12}$, nitrogen, —$NR^{14}$, sulfur, oxygen, selenium, phosphorous, silicon, arsenic, amido, C═C, $CR^{12}$-$CR^{13}$, $NR^{14}$-$NR^{15}$, or S—S;

Z is independently carbon, —$CR^{12}$, nitrogen, —$NR^{14}$, sulfur, oxygen, selenium, phosphorous, silicon, arsenic, amido, C═C, $CR^{12}$-$CR^{13}$, $NR^{14}$-$NR^{15}$, or S—S;

wherein at least one of X, Y and Z is other than carbon or C═C;

$R^{12}$ is hydrogen, alkyl, substituted alkyl, alkoxy, hydroxy, sulfo, halogen, amino, substituted amino, aldehyde, carboxylic acid, ester, azido, nitro, nitroso, cyano, or thioether;

$R^{13}$ is hydrogen, alkyl, substituted alkyl, alkoxy, hydroxy, sulfo, halogen, amino, substituted amino, aldehyde, carboxylic acid, ester, azido, nitro, nitroso, cyano, or thioether;

$R^{14}$ is hydrogen, alkyl, substituted alkyl, alkoxy, hydroxy, sulfo, halogen, amino, substituted amino, aldehyde, carboxylic acid, ester, azido, nitro, nitroso, cyano, or thioether;

$R^{15}$ is hydrogen, alkyl, substituted alkyl, alkoxy, hydroxy, sulfo, halogen, amino, substituted amino, aldehyde, carboxylic acid, ester, azido, nitro, nitroso, cyano, or thioether;

$R^1$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^1$ comprises a reactive group, carrier molecule or solid support $R^2$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^2$ comprises a reactive group, carrier molecule or solid support;

$R^3$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^3$ comprises a reactive group, carrier molecule or solid support;

$R^4$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^4$ comprises a reactive group, carrier molecule or solid support;

$R^5$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^5$ comprises a reactive group, carrier molecule or solid support;

$R^6$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^6$ comprises a reactive group, carrier molecule or solid support;

$R^7$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^7$ comprises a reactive group, carrier molecule or solid support;

$R^8$ is hydrogen, alkyl, substituted alkyl, 5-, 6- or 7-aromatic or heteroaromatic ring, substituted 5-, 6- or 7-aromatic or heteroaromatic ring or $R^8$ comprises a reactive group, carrier molecule or solid support;

$R^9$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^9$ comprises a reactive group, carrier molecule or solid support;

$R^{10}$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^{10}$ comprises a reactive group, carrier molecule or solid support; or a member selected from
  $R^1$ in combination with $R^2$;
  $R^2$ in combination with $R^3$;
  $R^3$ in combination with $R^4$;
  $R^4$ in combination with $R^5$;
  $R^6$ in combination with $R^7$
  $R^7$ in combination with $R^8$;
  $R^8$ in combination with $R^9$; and
  $R^9$ in combination with $R^{10}$;
  together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl.

The compounds/embodiments of the invention do not include Cascade Yellow:

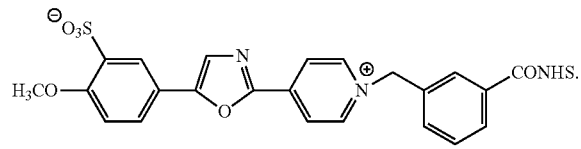

The middle ring structure of the Cascade Compound is an oxazole ring, however, additional rings will also provide desirable dye compounds, as presently described. Thus, any 5-, 6- or 7-membered heteroaryl ring, substituted or unsubstituted, is envisioned for this moiety of the compounds. In particular, X, Y and Z are independently carbon, —$CR^{12}$, nitrogen, —$NR^{14}$, sulfur, oxygen, selenium, phosphorous, silicon, arsenic, amido, C—C, $CR^{12}$-$CR^{13}$, $NR^{14}$-$NR^{15}$, or S—S, wherein at least one of X, Y and Z is other than carbon or C—C.

$R^{12}$-$R^{15}$ are independently hydrogen, alkyl, substituted alkyl, alkoxy, hydroxy, sulfo, halogen, amino, substituted amino, aldehyde, carboxylic acid, ester, azido, nitro, nitroso, cyano, or thioether.

$R^1$-$R^7$ and $R^9$-$R^{10}$ are independently hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or $R^1$-$R^7$ and $R^9$-$R^{10}$ independently comprises a reactive group, carrier molecule or solid support. $R^8$ is hydrogen, alkyl, substituted alkyl, 5-, 6- or 7-aromatic or heteroaromatic ring, substituted 5-, 6- or 7-aromatic or heteroaromatic ring or $R^8$ comprises a reactive group, carrier molecule or solid support.

Alternatively, or in addition to any of the above substituents, one or more of adjacent $R^1$-$R^{10}$ form a fused ring structure. Thus, in one aspect a member selected from $R^1$ in combination with $R^2$; $R^2$ in combination with $R^3$; $R^3$ in combination with $R^4$; $R^4$ in combination with $R^5$; $R^6$ in combination with $R^7$; $R^7$ in combination with $R^8$; $R^8$ in combination with $R^9$; and $R^9$ in combination with $R^{10}$; together with the atoms to which they are joined, form a ring which is a 5-, 6- or 7-membered cycloalkyl, a substituted 5-, 6- or 7-membered cycloalkyl, a 5-, 6- or 7-membered heterocycloalkyl, a substituted 5-, 6- or 7-membered heterocycloalkyl, a 5-, 6- or 7-membered aryl, a substituted 5-, 6- or 7-membered aryl, a 5-, 6- or 7-membered heteroaryl, or a substituted 5-, 6- or 7-membered heteroaryl.

In another more particular embodiment $R^8$ is alkyl substituted with —OR', =O, =NR', =N—OR', —NR'R", —SR', -halogen, —SiR'R"R''', —OC(O)R', —C(O)R', —CO2R', —CONR'R", —OC(O)NR'R", —NR"C(O)R', —NR'—C(O)NR"R''', —NR"C(O)2R', —NR—C(NR'R"R''')=NR'''', —NR—C(NR'R")=NR''', —S(O)R', —S(O)2R', —S(O)2NR'R", —NRSO2R', —CN and —NO2; wherein R', R", R''' and R'''' each independently are selected from the group consisting of hydrogen, substituted or unsubstituted heteroalkyl, substituted or unsubstituted aryl, substituted or unsubstituted alkyl, alkoxy, thioalkoxy and arylalkyl.

In a more particular embodiment still $R^8$ is —$(CH_2)_3SO_3^-$.

In another embodiment $R^8$ has the formula -L-$R^{8a}$, wherein L is absent or a divalent radical selected from the group consisting of alkyl, carbonyl, amino, thio or sulfo; and $R^{8a}$ is selected from the group consisting of H, substituted or unsubstituted aryl, substituted or unsubstituted heterocyclyl, substituted or unsubstituted heteroaryl, —$SO_3^-$, sulfo, sulfonamide, —CN, amino, nitro, halo, hydroxyl, alkoxy, carbonyl, carbonyloxy, aminocarbonyl, carbonylamino, and alkyl; provided $R^{8a}$ is not —$CH_2$—$(C_6H_5)$—CONHS.

More particularly, $R^{8a}$ is alkyl or aryl substituted with at least one —$SO_3^-$. In a more particular embodiment thereof $R^8$ is -alkyl-$SO_3$.

In another embodiment X is —$CR^{12}$ (i.e. =C($R^{12}$)—), Y is nitrogen, and Z is oxygen. More particularly $R^{12}$ is hydrogen.

In another embodiment $R^4$ is —$SO3^-$.

In another embodiment $R^3$ is a reactive group.

In another embodiment $R^3$ is alkoxy.

Particularly preferred are the compounds having the structure:

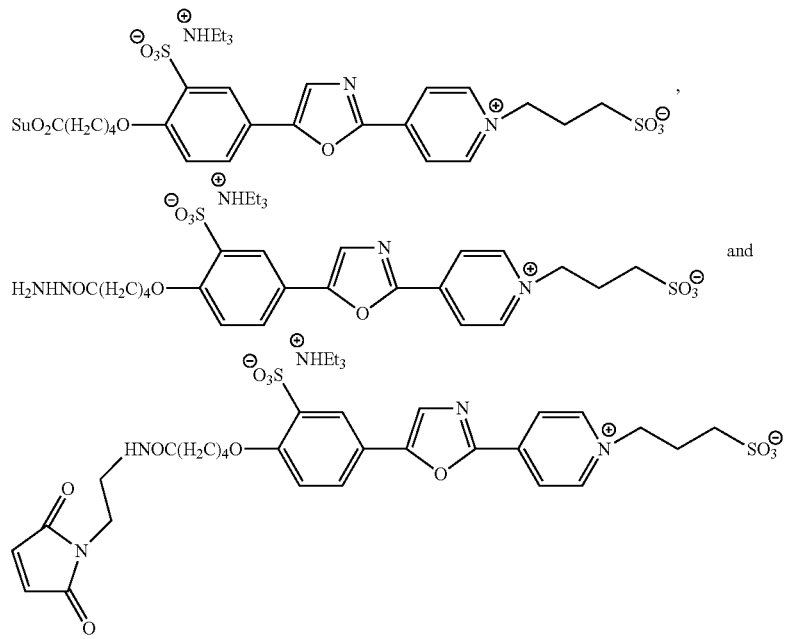

-continued

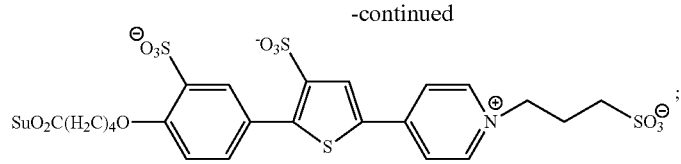

wherein, Su is succinimidyl.

Reactive Groups

In another exemplary embodiment of the invention, the present compounds are chemically reactive, and are substituted by at least one reactive group. The reactive group functions as the site of attachment for another moiety, such as a carrier molecule or a solid support, wherein the reactive group chemically reacts with an appropriate reactive or functional group on the carrier molecule or solid support. Thus, in another aspect of the present invention the compounds comprise the chelating moiety, linker, reporter moiety, a reactive group moiety and optionally a carrier molecule and/or a solid support.

In an exemplary embodiment, the compounds of the invention further comprise a reactive group which is a member selected from an acrylamide, an activated ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a photoactivatable group, a reactive platinum complex, a silyl halide, a sulfonyl halide, and a thiol. In a particular embodiment the reactive group is selected from the group consisting of carboxylic acid, succinimidyl ester of a carboxylic acid, hydrazide, amine and a maleimide. In exemplary embodiment, at least one member selected from $R^1$, $R^2$, $R^3$, $R^4$, $R^5$, $R^6$, $R^7$, $R^9$, $R^{10}$, and $R^{11}$, comprises a reactive group. Preferably, at least one of $R^1$, $R^2$, $R^3$, $R^4$ and $R^5$ comprises a reactive group. Alternatively, if the present compound comprises a carrier molecule or solid support a reactive group may be covalently attached independently to those substituents, allowing for further conjugation to a reporter molecule, carrier molecule or solid support.

In one aspect, the compound comprises at least one reactive group that selectively reacts with an amine group. This amine-reactive group is selected from the group consisting of succinimidyl ester, sulfonyl halide, tetrafluorophenyl ester and iosothiocyanates. Thus, in one aspect, the present compounds form a covalent bond with an amine containing molecule in a sample. In another aspect, the compound comprises at least one reactive group that selectively reacts with a thiol group. This thiol-reactive group is selected from the group consisting of maleimide, haloalkyl and haloacetamide (including any reactive groups disclosed in U.S. Pat. Nos. 5,362,628; 5,352,803 and 5,573,904).

These reactive groups are synthesized during the formation of the present compound and carrier molecule and solid support containing compounds to provide chemically reactive dyes. In this way, compounds incorporating a reactive group can be covalently attached to a wide variety of carrier molecules or solid supports that contain or are modified to contain functional groups with suitable reactivity, resulting in chemical attachment of the components. In an exemplary embodiment, the reactive group of the compounds of the invention and the functional group of the carrier molecule or solid support comprise electrophiles and nucleophiles that can generate a covalent linkage between them. Alternatively, the reactive group comprises a photoactivatable group, which becomes chemically reactive only after illumination with light of an appropriate wavelength. Typically, the conjugation reaction between the reactive group and the carrier molecule or solid support results in one or more atoms of the reactive group being incorporated into a new linkage attaching the present compound of the invention to the carrier molecule or solid support. Selected examples of functional groups and linkages are shown in Table 1, where the reaction of an electrophilic group and a nucleophilic group yields a covalent linkage.

TABLE 1

Examples of some routes to useful covalent linkages

| Electrophilic Group | Nucleophilic Group | Resulting Covalent Linkage |
|---|---|---|
| activated esters* | amines/anilines | carboxamides |
| acrylamides | thiols | thioethers |
| acyl azides** | amines/anilines | carboxamides |
| acyl halides | amines/anilines | carboxamides |
| acyl halides | alcohols/phenols | esters |
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

TABLE 1-continued

Examples of some routes to useful covalent linkages

| Electrophilic Group | Nucleophilic Group | Resulting Covalent Linkage |
|---|---|---|
| Inorganic azide or alkyl azide | phosphine | Amide bond |

*Activated esters, as understood in the art, generally have the formula —COΩ, where Ω is a good leaving group (e.g., succinimidyloxy (—OC$_4$H$_4$O$_2$) sulfosuccinimidyloxy (—OC$_4$H$_3$O$_2$—SO$_3$H), -1-oxybenzotriazolyl (—OC$_6$H$_4$N$_3$); or an aryloxy group or aryloxy substituted one or more times by electron withdrawing substituents such as nitro, fluoro, chloro, cyano, or trifluoromethyl, or combinations thereof, used to form activated aryl esters; or a carboxylic acid activated by a carbodiimide to form an anhydride or mixed anhydride —OCOR$^a$ or —OCNR$^a$NHR$^b$, where R$^a$ and R$^b$, which may be the same or different, are C$_1$-C$_6$ alkyl, C$_1$-C$_6$ perfluoroalkyl, or C$_1$-C$_6$ alkoxy; or cyclohexyl, 3-dimethylaminopropyl, or N-morpholinoethyl).
**Acyl azides can also rearrange to isocyanates In some embodiments, the reactive group further comprises a linker, L, in addition to the reactive functional moiety. The linker is used to covalently attach a reactive functional moiety to the 3-alkoxy xanthene dye/biological moiety compound of the invention. When present, the linker is a single covalent bond or a series of stable bonds. Thus, the reactive functional moiety may be directly attached (where the linker is a single bond) to the 3-alkoxy xanthene/biological moiety compounds or attached through a series of stable bonds. When the linker is a series of stable covalent bonds the linker typically incorporates 1-20 nonhydrogen atoms selected from the group consisting of C, N, O, S, and P. In addition, the covalent linkage can incorporate a platinum atom, such as described in U.S. Pat. No. 5,714,327. When the linker is not a single covalent bond, the linker may be any combination of stable chemical bonds, optionally including, single, double, triple or aromatic carbon-carbon bonds, as well as carbon-nitrogen bonds, nitrogen-nitrogen bonds, carbon-oxygen bonds, sulfur-sulfur bonds, carbon-sulfur bonds, phosphorus-oxygen bonds, phosphorus-nitrogen bonds, and nitrogen-platinum bonds. In an exemplary embodiment, the linker incorporates less than 15 nonhydrogen atoms and are composed of a combination of ether, thioether, thiourea, amine, ester, carboxamide, sulfonamide, hydrazide bonds and aromatic or heteroaromatic bonds. Typically the linker is a single covalent bond or a combination of single carbon-carbon bonds and carboxamide, sulfonamide or thioether bonds. The following moieties can be found in the linker: ether, thioether, carboxamide, thiourea, sulfonamide, urea, urethane, hydrazine, alkyl, aryl, heteroaryl, alkoxy, cycloalkyl and amine moieties. Examples of L include substituted or unsubstituted polymethylene, arylene, alkylarylene, arylenealkyl, or arylthio.

Any combination of linkers may be used to attach the reactive groups and the present compounds together, typically a compound of the present invention when attached to more than one reactive group will have one or two linkers attached that may be the same or different. The linker may also be substituted to alter the physical properties of the present compounds, such as solubility and spectral properties of the compound.

Choice of the reactive group used to attach the compound of the invention to the substance to be conjugated typically depends on the reactive or functional group on the substance to be conjugated and the type or length of covalent linkage desired. The types of functional groups typically present on the organic or inorganic substances (biomolecule or nonbiomolecule) include, but are not limited to, amines, amides, thiols, alcohols, phenols, aldehydes, ketones, phosphates, imidazoles, hydrazines, hydroxylamines, disubstituted amines, halides, epoxides, silyl halides, carboxylate esters, sulfonate esters, purines, pyrimidines, carboxylic acids, olefinic bonds, or a combination of these groups. A single type of reactive site may be available on the substance (typical for polysaccharides or silica), or a variety of sites may occur (e.g., amines, thiols, alcohols, phenols), as is typical for proteins.

Typically, the reactive group will react with an amine, a thiol, an alcohol, an aldehyde, a ketone, or with silica. Preferably, reactive groups react with an amine or a thiol functional group, or with silica. In one embodiment, the reactive group is an acrylamide, an activated ester of a carboxylic acid, an acyl azide, an acyl nitrile, an aldehyde, an alkyl halide, a silyl halide, an anhydride, an aniline, an aryl halide, an azide, an aziridine, a boronate, a diazoalkane, a haloacetamide, a halotriazine, a hydrazine (including hydrazides), an imido ester, an isocyanate, an isothiocyanate, a maleimide, a phosphoramidite, a reactive platinum complex, a sulfonyl halide, or a thiol group. By "reactive platinum complex" is particularly meant chemically reactive platinum complexes such as described in U.S. Pat. No. 5,714,327.

Where the reactive group is an activated ester of a carboxylic acid, such as a succinimidyl ester of a carboxylic acid, a sulfonyl halide, a tetrafluorophenyl ester or an isothiocyanates, the resulting compound is particularly useful for preparing conjugates of carrier molecules such as proteins, nucleotides, oligonucleotides, or haptens. Where the reactive group is a maleimide, haloalkyl or haloacetamide (including any reactive groups disclosed in U.S. Pat. Nos. 5,362,628; 5,352, 803 and 5,573,904 (supra)) the resulting compound is particularly useful for conjugation to thiol-containing substances. Where the reactive group is a hydrazide, the resulting compound is particularly useful for conjugation to periodate-oxidized carbohydrates and glycoproteins, and in addition is an aldehyde-fixable polar tracer for cell microinjection. Where the reactive group is a silyl halide, the resulting compound is particularly useful for conjugation to silica surfaces, particularly where the silica surface is incorporated into a fiber optic probe subsequently used for remote ion detection or quantitation.

In a particular aspect, the reactive group is a photoactivatable group such that the group is only converted to a reactive species after illumination with an appropriate wavelength. An appropriate wavelength is generally a UV wavelength that is less than 400 nm. This method provides for specific attachment to only the target molecules, either in solution or immobilized on a solid or semi-solid matrix. Photoactivatable reactive groups include, without limitation, benzophenones, aryl azides and diazirines.

Preferably, the reactive group is a photoactivatable group, succinimidyl ester of a carboxylic acid, a haloacetamide, haloalkyl, a hydrazine, an isothiocyanate, a maleimide group, an aliphatic amine, a silyl halide, a cadaverine or a psoralen. More preferably, the reactive group is a succinimidyl ester of a carboxylic acid, a maleimide, an iodoacetamide, or a silyl halide. In a particular embodiment the reactive group is a succinimidyl ester of a carboxylic acid, a sulfonyl halide, a tetrafluorophenyl ester, an iosothiocyanates or a maleimide.

Carrier Molecules

In an exemplary embodiment is provided dyes covalently conjugated to a carrier molecule. This includes, but is not limited to, any combination of compounds disclosed above and any carrier molecule disclosed herein. Typically the compound comprises a reactive group that facilitates the covalent conjugation to the carrier molecule. The reactive group may contain both a reactive functional moiety and a linker, or only the reactive functional moiety.

Provided in one embodiment is a first composition that comprises a present compound, a first fluorophore, and a carrier molecule. Provided in another embodiment is a second composition that includes a first composition in combination with a second conjugate. The second conjugate comprises a carrier molecule or solid support, as disclosed below, that is covalently bonded to a second fluorophore. The first and second fluorophore have different structures and preferably have different emission spectra. Even more preferably, the first and second fluorophores are selected so that their fluorescence emissions essentially do not overlap. In another embodiment the fluorophores have different excitation spectra, alternatively the fluorophores are excited by the same laser.

The fluorophore on the second conjugate can include substantially any fluorescent structure known in the art including, but not limited to, small organic fluorophores, fluorescent proteins, and reporter groups that are not necessarily fluorescent but which, under correct conditions, convert a fluorogenic substrate into a fluorophore, e.g., horseradish peroxidase. Exemplary second fluorophores of use in the present invention include those that include a moiety that is a member selected from a coumarin, a xanthene (e.g., fluorescein), a cyanine, a pyrene, a borapolyazaindacene, an oxazine, and bimane.

The carrier molecule (or solid support) of the conjugates in the second composition may be the same or a different molecule. The discussion herein pertaining to the identity of various carrier molecules is generally applicable to this embodiment of the invention as well as other embodiments.

A variety of carrier molecules are useful in the present invention. Exemplary carrier molecules include antigens, steroids, vitamins, drugs, haptens, metabolites, toxins, environmental pollutants, amino acids, peptides, proteins, nucleic acids, nucleic acid polymers, carbohydrates, lipids, and polymers. In another exemplary embodiment, at least one member selected from $R^1$, $R^2$, $R^3$, $R^4$, $R^5$, $R^6$, $R^7$, $R^9$, and $R^{10}$ comprises a carrier molecule or is attached to a carrier molecule. In one aspect at least one of $R^1$, $R^2$, $R^3$, and $R^4$ comprises a carrier molecule or is attached to a carrier molecule.

In an exemplary embodiment, the carrier molecule comprises an amino acid, a peptide, a protein, a polysaccharide, a nucleoside, a nucleotide, an oligonucleotide, a nucleic acid, a hapten, a psoralen, a drug, a hormone, a lipid, a lipid assembly, a synthetic polymer, a polymeric microparticle, a biological cell, a virus and combinations thereof. In another exemplary embodiment, the carrier molecule is selected from a hapten, a nucleotide, an oligonucleotide, a nucleic acid polymer, a protein, a peptide or a polysaccharide. In a preferred embodiment the carrier molecule is amino acid, a peptide, a protein, a polysaccharide, a nucleoside, a nucleotide, an oligonucleotide, a nucleic acid, a hapten, a psoralen, a drug, a hormone, a lipid, a lipid assembly, a tyramine, a synthetic polymer, a polymeric microparticle, a biological cell, cellular components, an ion chelating moiety, an enzymatic substrate or a virus. In another preferred embodiment, the carrier molecule is an antibody or fragment thereof, an antigen, an avidin or streptavidin, a biotin, a dextran, an IgG binding protein, a fluorescent protein, agarose, and a non-biological microparticle.

In some embodiments, the carrier molecule may include a carrier molecule reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the carrier molecule reactive functional groups herein.

In an exemplary embodiment, the enzymatic substrate is selected from an amino acid, peptide, sugar, alcohol, alkanoic acid, 4-guanidinobenzoic acid, nucleic acid, lipid, sulfate, phosphate, $-CH^2POCOalkyl$ and combinations thereof. Thus, the enzyme substrates can be cleaved by enzymes selected from the group consisting of peptidase, phosphatase, glycosidase, dealkylase, esterase, guanidinobenzotase, sulfatase, lipase, peroxidase, histone deacetylase, endoglycoceramidase, exonuclease, reductase and endonuclease.

In another exemplary embodiment, the carrier molecule is an amino acid (including those that are protected or are substituted by phosphates, carbohydrates, or $C_1$ to $C_{22}$ carboxylic acids), or a polymer of amino acids such as a peptide or protein. In a related embodiment, the carrier molecule contains at least five amino acids, more preferably 5 to 36 amino acids. Exemplary peptides include, but are not limited to, neuropeptides, cytokines, toxins, protease substrates, and protein kinase substrates. Other exemplary peptides may function as organelle localization peptides, that is, peptides that serve to target the conjugated compound for localization within a particular cellular substructure by cellular transport mechanisms. Preferred protein carrier molecules include enzymes, antibodies, lectins, glycoproteins, histones, albumins, lipoproteins, avidin, streptavidin, protein A, protein G, phycobiliproteins and other fluorescent proteins, hormones, toxins and growth factors. Typically, the protein carrier molecule is an antibody, an antibody fragment, avidin, streptavidin, a toxin, a lectin, or a growth factor. Exemplary haptens include biotin, digoxigenin and fluorophores.

In another exemplary embodiment, the carrier molecule comprises a nucleic acid base, nucleoside, nucleotide or a nucleic acid polymer, optionally containing an additional linker or spacer for attachment of a fluorophore or other ligand, such as an alkynyl linkage (U.S. Pat. No. 5,047,519), an aminoallyl linkage (U.S. Pat. No. 4,711,955) or other linkage. In another exemplary embodiment, the nucleotide carrier molecule is a nucleoside or a deoxynucleoside or a dideoxynucleoside.

Exemplary nucleic acid polymer carrier molecules are single- or multi-stranded, natural or synthetic DNA or RNA oligonucleotides, or DNA/RNA hybrids, or incorporating an unusual linker such as morpholine derivatized phosphates (AntiVirals, Inc., Corvallis Oreg.), or peptide nucleic acids such as N-(2-aminoethyl)glycine units, where the nucleic acid contains fewer than 50 nucleotides, more typically fewer than 25 nucleotides.

In another exemplary embodiment, the carrier molecule comprises a carbohydrate or polyol that is typically a polysaccharide, such as dextran, FICOLL, heparin, glycogen, amylopectin, mannan, inulin, starch, agarose and cellulose, or is a polymer such as a polyethylene glycol). In a related embodiment, the polysaccharide carrier molecule includes dextran, agarose or FICOLL.

In another exemplary embodiment, the carrier molecule comprises a lipid (typically having 6-25 carbons), including glycolipids, phospholipids, and sphingolipids. Alternatively, the carrier molecule comprises a lipid vesicle, such as a liposome, or is a lipoprotein (see below). Some lipophilic substituents are useful for facilitating transport of the conjugated dye into cells or cellular organelles.

Alternatively, the carrier molecule is a cell, cellular systems, cellular fragment, or subcellular particles, including virus particles, bacterial particles, virus components, biological cells (such as animal cells, plant cells, bacteria, or yeast), or cellular components. Examples of cellular components that are useful as carrier molecules include lysosomes, endosomes, cytoplasm, nuclei, histones, mitochondria, Golgi apparatus, endoplasmic reticulum and vacuoles.

In another exemplary embodiment, the carrier molecule non-covalently associates with organic or inorganic materials. Exemplary embodiments of the carrier molecule that possess a lipophilic substituent can be used to target lipid assemblies such as biological membranes or liposomes by non-covalent incorporation of the dye compound within the membrane, e.g., for use as probes for membrane structure or for incorporation in liposomes, lipoproteins, films, plastics, lipophilic microspheres or similar materials.

In an exemplary embodiment, the carrier molecule comprises a specific binding pair member wherein the present compounds are conjugated to a specific binding pair member and used to the formation of the bound pair. Alternatively, the presence of the labeled specific binding pair member indicates the location of the complementary member of that specific binding pair; each specific binding pair member having an area on the surface or in a cavity which specifically binds to, and is complementary with, a particular spatial and polar organization of the other. In this instance, the dye compounds of the present invention function as a reporter molecule for the specific binding pair. Exemplary binding pairs are set forth in Table 2.

TABLE 2

Representative Specific Binding Pairs

| antigen | antibody |
| --- | --- |
| biotin | avidin (or streptavidin or anti-biotin) |
| IgG* | protein A or protein G |
| drug | drug receptor |
| folate | folate binding protein |
| toxin | toxin receptor |
| carbohydrate | lectin or carbohydrate receptor |
| peptide | peptide receptor |
| protein | protein receptor |
| enzyme substrate | enzyme |
| DNA (RNA) | cDNA (cRNA)† |
| hormone | hormone receptor |
| ion | chelator |

*IgG is an immunoglobulin
†cDNA and cRNA are the complementary strands used for hybridization In a particular aspect the carrier molecule is an antibody fragment, such as, but not limited to, anti-Fc, an anti-Fc isotype, anti-J chain, anti-kappa light chain, anti-lambda light chain, or a single-chain fragment variable protein; or a non-antibody peptide or protein, such as, for example but not limited to, soluble Fc receptor, protein G, protein A, protein L, lectins, or a fragment thereof. In one aspect the carrier molecule is a Fab fragment specific to the Fc portion of the target-binding antibody or to an isotype of the Fc portion of the target-binding antibody (U.S. Ser. No. 10/118,204). The monovalent Fab fragments are typically produced from either murine monoclonal antibodies or polyclonal antibodies generated in a variety of animals, for example but not limited to, rabbit or goat. These fragments can be generated from any isotype such as murine IgM, $IgG_1$, $IgG_{2a}$, $IgG_{2b}$ or $IgG_3$.

Alternatively, a non-antibody protein or peptide such as protein G, or other suitable proteins, can be used alone or coupled with albumin. Preferred albumins include human and bovine serum albumins or ovalbumin. Protein A, G and L are defined to include those proteins known to one skilled in the art or derivatives thereof that comprise at least one binding domain for IgG, i.e. proteins that have affinity for IgG. These proteins can be modified but do not need to be and are conjugated to a reactive label in the same manner as the other carrier molecules of the invention.

In another aspect the carrier molecule is a whole intact antibody. Antibody is a term of the art denoting the soluble substance or molecule secreted or produced by an animal in response to an antigen, and which has the particular property of combining specifically with the antigen that induced its formation. Antibodies themselves also serve are antigens or immunogens because they are glycoproteins and therefore are used to generate antispecies antibodies. Antibodies, also known as immunoglobulins, are classified into five distinct classes—IgG, IgA, IgM, IgD, and IgE. The basic IgG immunoglobulin structure consists of two identical light polypeptide chains and two identical heavy polypeptide chains (linked together by disulfide bonds).

When IgG is treated with the enzyme papain a monovalent antigen-binding fragment can be isolated, referred herein to as a Fab fragment. When IgG is treated with pepsin (another proteolytic enzyme), a larger fragment is produced, F(ab')$_2$. This fragment can be split in half by treating with a mild reducing buffer that results in the monovalent Fab' fragment. The Fab' fragment is slightly larger than the Fab and contains one or more free sulfhydryls from the hinge region (which are not found in the smaller Fab fragment). The term "antibody fragment" is used herein to define the Fab', F(ab')$_2$ and Fab portions of the antibody. It is well known in the art to treat antibody molecules with pepsin and papain in order to produce antibody fragments (Gorevic et al., Methods of Enzyol., 116:3 (1985)).

The monovalent Fab fragments of the present invention are produced from either murine monoclonal antibodies or polyclonal antibodies generated in a variety of animals that have been immunized with a foreign antibody or fragment thereof, U.S. Pat. No. 4,196,265 discloses a method of producing monoclonal antibodies. Typically, secondary antibodies are derived from a polyclonal antibody that has been produced in a rabbit or goat but any animal known to one skilled in the art to produce polyclonal antibodies can be used to generate anti-species antibodies. The term "primary antibody" describes an antibody that binds directly to the antigen as opposed to a "secondary antibody" that binds to a region of the primary antibody. Monoclonal antibodies are equal, and in some cases, preferred over polyclonal antibodies provided that the ligand-binding antibody is compatible with the monoclonal antibodies that are typically produced from murine hybridoma cell lines using methods well known to one skilled in the art.

In one aspect the antibodies are generated against only the Fc region of a foreign antibody. Essentially, the animal is immunized with only the Fc region fragment of a foreign antibody, such as murine. The polyclonal antibodies are collected from subsequent bleeds, digested with an enzyme, pepsin or papain, to produce monovalent fragments. The fragments are then affinity purified on a column comprising whole immunoglobulin protein that the animal was immunized against or just the Fc fragments.

Solid Supports

In an exemplary embodiment is provided dyes covalently conjugated to a solid support. This includes, but is not limited to, any combination of compounds disclosed above and any solid support disclosed herein. Typically the compound comprises a reactive group that facilitates the covalent conjugation to the solid support. The reactive group may contain both a reactive functional moiety and a linker, or only the reactive functional moiety.

Provided in one embodiment is a first composition that comprises a present compound, a first fluorophore, and a solid support. Provided in another embodiment is a second composition that includes a first composition in combination with a second conjugate. The second conjugate comprises a solid support or carrier molecule, as disclosed above, that is covalently bonded to a second fluorophore. The first and second fluorophore have different structures and preferably have different emission spectra. Even more preferably, the first and second fluorophores are selected so that their fluorescence emissions essentially do not overlap. In another embodiment the fluorophores have different excitation spectra, alternatively the fluorophores are excited by the same laser.

The fluorophore on the second conjugate can include substantially any fluorescent structure known in the art including, but not limited to, small organic fluorophores, fluorescent proteins, and reporter groups that are not necessarily fluorescent but which, under correct conditions, convert a fluorogenic substrate into a fluorophore, e.g., horseradish peroxidase. Exemplary second fluorophores of use in the present invention include those that include a moiety that is a member selected from a coumarin, a xanthene (e.g., fluorescein), a cyanine, a pyrene, a borapolyazaindacene, an oxazine, and bimane.

The solid support (or carrier molecule) of the conjugates in the second composition may be the same or a different molecule. The discussion herein pertaining to the identity of various solid supports is generally applicable to this embodiment of the invention as well as other embodiments.

A variety of solid supports are useful in the present invention. In an exemplary embodiment, the present compounds of the invention are covalently bonded to a solid support. The solid support may be attached to the compound through the reactive group, if present, or through a carrier molecule, if present. In another exemplary embodiment, at least one member selected from $R^1, R^2, R^3, R^4, R^5, R^6, R^7, R^9, R^{10}$, and $R^{11}$, comprises a solid support or is attached to a solid support. In one aspect, at least one of $R^1, R^2, R^3, R^4$, or $R^5$, comprises a solid support or is attached to a solid support.

A solid support suitable for use in the present invention is typically substantially insoluble in liquid phases. Solid supports of the current invention are not limited to a specific type of support. Rather, a large number of supports are available and are known to one of ordinary skill in the art. Thus, useful solid supports include solid and semi-solid matrixes, such as aerogels and hydrogels, resins, beads, biochips (including thin film coated biochips), microfluidic chip, a silicon chip, multi-well plates (also referred to as microtitre plates or microplates), membranes, conducting and nonconducting metals, glass (including microscope slides) and magnetic supports. More specific examples of useful solid supports include silica gels, polymeric membranes, particles, derivatized plastic films, glass beads, cotton, plastic beads, alumina gels, polysaccharides such as Sepharose, poly(acrylate), polystyrene, poly(acrylamide), polyol, agarose, agar, cellulose, dextran, starch, FICOLL, heparin, glycogen, amylopectin, mannan, inulin, nitrocellulose, diazocellulose, polyvinylchloride, polypropylene, polyethylene (including poly (ethylene glycol)), nylon, latex bead, magnetic bead, paramagnetic bead, superparamagnetic bead, starch and the like.

In some embodiments, the solid support may include a solid support reactive functional group, including, but not limited to, hydroxyl, carboxyl, amino, thiol, aldehyde, halogen, nitro, cyano, amido, urea, carbonate, carbamate, isocyanate, sulfone, sulfonate, sulfonamide, sulfoxide, etc., for attaching the compounds of the invention. Useful reactive groups are disclosed above and are equally applicable to the solid support reactive functional groups herein.

A suitable solid phase support can be selected on the basis of desired end use and suitability for various synthetic protocols. For example, where amide bond formation is desirable to attach the compounds of the invention to the solid support, resins generally useful in peptide synthesis may be employed, such as polystyrene (e.g., PAM-resin obtained from Bachem Inc., Peninsula Laboratories, etc.), POLYHIPE™ resin (obtained from Aminotech, Canada), polyamide resin (obtained from Peninsula Laboratories), polystyrene resin grafted with polyethylene glycol (TentaGel™, Rapp Polymere, Tubingen, Germany), polydimethyl-acrylamide resin (available from Milligen/Biosearch, California), or PEGA beads (obtained from Polymer Laboratories).

Preparation of Conjugates

In another embodiment is provided a method for forming conjugates of the present dye compounds and a carrier molecule or solid support. This method comprises:
a) combining a present compound with a carrier molecule or solid support to form a combined sample, wherein the compound comprises a reactive group; and,
b) incubating the combined sample for a sufficient amount of time for the compound to form a covalent bond with either the carrier molecule or solid support whereby a dye conjugate is formed.

The dye conjugates of the carrier molecules or solid supports, e.g., drugs, peptides, toxins, nucleotides, phospholipids and other organic molecules are prepared by organic synthesis methods using the reactive dyes of the invention and are generally prepared by means well recognized in the art (Haugland, MOLECULAR PROBES HANDBOOK, supra, (2002)). Preferably, conjugation to form a covalent bond consists of simply mixing the reactive compounds of the present invention in a suitable solvent in which both the reactive compound and the substance to be conjugated are soluble. The reaction preferably proceeds spontaneously without added reagents at room temperature or below. For those reactive compounds that are photoactivated, conjugation is facilitated by illumination of the reaction mixture to activate the reactive compound. Chemical modification of water-insoluble substances, so that a desired compound-conjugate may be prepared, is preferably performed in an aprotic solvent such as dimethylformamide, dimethylsulfoxide, acetone, ethyl acetate, toluene, or chloroform. Similar modification of water-soluble materials is readily accomplished through the use of the instant reactive compounds to make them more readily soluble in organic solvents.

Preparation of peptide or protein conjugates typically comprises first dissolving the protein to be conjugated in aqueous buffer at about 1-10 mg/mL at room temperature or below. Bicarbonate buffers (pH about 8.3) are especially suitable for reaction with succinimidyl esters, phosphate buffers (pH about 7.2-8) for reaction with thiol-reactive functional groups and carbonate or borate buffers (pH about 9) for reaction with isothiocyanates and dichlorotriazines. The appropriate reactive compound is then dissolved in a nonhydroxylic solvent (usually DMSO or DMF) in an amount sufficient to give a suitable degree of conjugation when added to a solution of the protein to be conjugated. The appropriate amount of compound for any protein or other component is conveniently predetermined by experimentation in which variable amounts of the compound are added to the protein, the conjugate is chromatographically purified to separate unconjugated compound and the compounde-protein conjugate is tested in its desired application.

Following addition of the reactive compound to the component solution, the mixture is incubated for a suitable period (typically about 1 hour at room temperature to several hours on ice), the excess compound is removed by gel filtration, dialysis, HPLC, adsorption on an ion exchange or hydrophobic polymer or other suitable means. The compound-conjugate is used in solution or lyophilized. In this way, suitable conjugates can be prepared from antibodies, antibody fragments, avidins, lectins, enzymes, proteins A and G, cellular proteins, albumins, histones, growth factors, hormones, and other proteins.

Conjugates of polymers, including biopolymers and other higher molecular weight polymers are typically prepared by means well recognized in the art (for example, Brinkley et al., *Bioconjugate Chem.*, 3: 2 (1992)). In these embodiments, a single type of reactive site may be available, as is typical for polysaccharides) or multiple types of reactive sites (e.g. amines, thiols, alcohols, phenols) may be available, as is typical for proteins. Selectivity of labeling is best obtained by selection of an appropriate reactive dye. For example, modification of thiols with a thiol-selective reagent such as a haloacetamide or maleimide, or modification of amines with an amine-reactive reagent such as an activated ester, acyl azide, isothiocyanate or 3,5-dichloro-2,4,6-triazine. Partial selectivity can also be obtained by careful control of the reaction conditions.

When modifying polymers with the compounds, an excess of compound is typically used, relative to the expected degree of compound substitution. Any residual, unreacted compound or a compound hydrolysis product is typically removed by dialysis, chromatography or precipitation. Presence of residual, unconjugated dye can be detected by thin layer chromatography using a solvent that elutes the dye away from its conjugate. In all cases it is usually preferred that the reagents be kept as concentrated as practical so as to obtain adequate rates of conjugation.

In an exemplary embodiment, the conjugate of the invention is associated with an additional substance, that binds either to the fluorophore or the conjugated substance (carrier molecule or solid support) through noncovalent interaction. In another exemplary embodiment, the additional substance is an antibody, an enzyme, a hapten, a lectin, a receptor, an oligonucleotide, a nucleic acid, a liposome, or a polymer. The additional substance is optionally used to probe for the location of the dye-conjugate, for example, as a means of enhancing the signal of the dye-conjugate.

Method of Use

The present invention also provides methods of using the compounds described herein to detect an analyte in a sample. Those of skill in the art will appreciate that this focus is for clarity of illustration and does not limit the scope of the methods in which the compounds of the invention find use.

In certain embodiments, the compounds of the present invention are utilized to stain a sample to give a detectable optical response under desired conditions by a) preparing a dye solution comprising a dye compound described above, at a concentration sufficient to yield a detectable optical response under the desired conditions; combining the sample of interest with the dye solution for a period of time sufficient for the dye compound to yield a detectable optical response under the desired conditions; and c) illuminating the sample at a wavelength selected to elicit the optical response. Optionally, the sample is washed to remove residual, excess or unbound dye. The dye compound typically forms a covalent or non-covalent association or complex with an element of the sample, or is simply present within the bounds of the sample or portion of the sample.

In one embodiment, the staining is used to determine a specified characteristic of the sample by further comparing the optical response with a standard or expected response. For example, the dye solution is used to monitor specific components of the sample with respect to their spatial and temporal distribution in the sample. Alternatively, the dye preferentially binds to a specific analyte in a sample, enabling the researcher to determine the presence or quantity of that specific analyte. In this instance the dye is typically conjugated to a carrier molecule or solid support that directly interacts with the analyte of interest. In this way the dye of the present invention is a reporter molecule. However, in certain circumstances the dye may bind directly, covalently or no-covalently, to an analyte of interest in the sample. The desired analysis to be performed determines the composition of the dye solution and chemical nature of the dye itself. In another example, the dye is bound by an antibody directed against the dye itself, typically resulting in the fluorescence quenching of the dye.

In another embodiment of the invention, the dye compounds of the invention possess utility as laser dyes according to methods known in the art. In particular, the dyes are excited by a UV or violet laser. This is particularly advantages for multiplexing wherein many known dyes are excited by wavelengths at 488 nm or longer. Thus, in one embodiment the present dyes are excited at about a 405 nm range but not at 488 nm or longer and their emission spectra is distinguishable from those dyes that are excited at longer wavelengths. These dyes have particular applications when analyzed by flow cytometry. In addition, these dyes also find use in applications with other dyes that are excited at about 400 nm because the long Stokes shift of the present compound allows for the detectable signal to be resolved compared to other dyes. Thus, in one aspect is a dye with a Stokes shift longer than about 50 nm, preferably more than about 100 nm, even more preferable longer than about 150 nm. In one aspect the present compounds have a Stokes shift of about 140 nm.

In one aspect of the invention is provided a method for detecting an analyte in a sample, wherein the method comprises:
 a. combining a present compound with a sample to form a combined sample;
 b. incubating the combined sample for a sufficient amount of time for the compound to associate with the analyte in the sample to form an incubated sample;
 c. illuminating the incubated sample with an appropriate wavelength to form an illuminated sample; and d. detecting the illuminated sample whereby the analyte in the sample is detected.

The combined sample of the conjugate and the analyte is incubated under any appropriate conditions for a length of time sufficient for at least a fraction of the analyte population to interact with the conjugate. The interaction can be by any known interaction mechanism, and the present invention is not limited to application with any single type of analyte-conjugate interaction mechanism. The interaction between the analyte and the conjugate results in the formation of a fluorescent analyte. The fluorescent analyte is readily detected and/or quantitated by irradiating it with light of a wavelength that causes the fluorescent analyte to emit fluorescence.

In one embodiment the dye is illuminated with a wavelength about 405 nm, common on violet lasers. In a particular aspect the illumination and/or detecting step comprises a flow cytometer.

In the method described above, any number or combination of purification, separation or derivatization steps are optionally included as steps in the method. In an exemplary embodiment, the fluorescent analyte is separated from the remainder of the sample, from non-fluorescent analyte or from excess unbound conjugate prior to determining the fluorescence of the fluorescent analyte.

In another exemplary embodiment, the invention provides a multicolor method for detecting an analyte or more than one analyte. For example, when it is desired to detect, and particularly to confirm the identity of an analyte, more than one fluorescent conjugate, preferably fluorescing at different wavelengths can be co-localized on the single analyte.

Therefore, a method for detecting a first analyte and a second analyte in a sample is provided. The method includes incubating the sample with a composition of the invention that includes first and second fluorescent labeled conjugates. The component of the first conjugate is a binding partner for the first analyte and the component of the second conjugate is a binding partner for the second analyte. The incubation continues for a time and under conditions appropriate to induce an interaction between at least a fraction of the population of the first analyte with the first conjugate. During this incubation period, it is generally preferred that a similar interaction occurs between the second analyte and second conjugate, however, it is within the scope of the invention to change the incubation conditions as necessary to drive the formation of a conjugate-analyte complex between the second conjugate and second analyte.

Following the formation of at least the first analyte-conjugate complex, the sample is illuminated with light of a wavelength appropriate to cause the complex to fluoresce, thereby detecting the first analyte. The second analyte is detected in a similar manner and may be detected simultaneously with the first analyte or by the sequential illumination of the sample with wavelengths appropriate to induce the fluorescence of each fluorescent conjugate. In another embodiment the use of more than one color of fluorescent conjugate per analyte provides assays in which specificity is dramatically increased, by requiring that the different colors or color combinations of the fluorescent conjugates coincide spatially during detection. This can dramatically reduce or even eliminate the detection of nonspecifically bound targets or labels, enhancing specificity and sensitivity of the assay. Underlying the improvement represented by the use of multiple differently colored fluorescent conjugates is the improbability of accidentally encountering two or more preselected different colors at the same location at the same time. The improbability increases as more fluorescent conjugates of different colors are used. Alternatively, in another exemplary embodiment, the emission from the two or more differently colored fluorescent conjugates combines to form a third color, which is not otherwise present in the assay.

In an exemplary application of the present method, different features of an analyte, e.g., a cell or epitopes of a molecule, are labeled with different colored fluorescent conjugates. The target is detected and its identity is confirmed using the colocalization or "coincidence" of each color on each target. Coincidence staining allows for the detection and differentiation of different organisms or strains of organisms expressing different surface markers. Moreover, coincidence staining provides a method of distinguishing molecules of different structure down to the level of isomeric differences and differences in stereochemistry.

In the detection of pathogenesis, the most direct analyte is the pathogenic organism itself. In this case, assays preferably identify particular features of the organism such as surface proteins. To further aid in characterization, it is preferred to assay for molecular analytes as well. An example of a molecular analyte is an exotoxin such as cholera toxin. Antigen specific binding receptors are generated that recognize different characteristics of an analyte with high specificity. In the case of molecular analytes, receptors recognize different epitopes of a protein or small molecule, while cellular analytes are recognized through different molecules on the cell surface.

Although the fluorescence from each conjugate can be detected simultaneously, in one embodiment, to facilitate coincidence staining, the fluorescence from each analyte is detected independently.

In another exemplary embodiment, colocalization is used to differentiate between the formation of an analyte-conjugate complex and non-specific binding of the analyte to another species within the assay system. The intrinsic sensitivity of an assay often is limited by nonspecific binding of the analyte or other assay mixture components to the substrate. Single analyte coincidence staining can be used to differentiate between specific binding of the analyte to the conjugate and non-specific binding of assay mixture components to the conjugate based on the colocalization of fluorescent conjugate colors. Those of skill in the art will appreciate that coincidence staining as described herein is useful to distinguish nonspecific binding in both solid-phase (e.g., gene chip) and solution-based assays.

Coincidence staining can also be used to identify a single analyte. For example, one may wish to confirm the presence of a selected analyte in a mixture of analytes that are structurally similar (e.g. having a common epitope) or that have similar affinity for the component of the conjugate. In such circumstances, it may prove that the detection of a single epitope is not sufficient for conclusive identification of a target. Measuring the level of 2, preferably 3, more preferably 4 and even more preferably 5 or more markers within a single analyte, provides an unambiguous profile specific for the analyte of interest.

In another exemplary embodiment, the present invention provides methods for evaluating cell viability. In this instance the present compounds that comprise an amine reactive group, meaning a reactive group that will form a covalent bond with an amine on a solid support or carrier molecule, are incubated with a sample comprising both live and dead cells. The present compounds will for conjugates with the amine groups on the membrane of live cells producing a fluorescent signal when illuminated with an appropriate light source. However, for dead cells the cell membrane has been compromised allowing entry of the compounds into the cells where they form conjugates with the amines in the cells. These conjugates in the dead cells produce a fluorescent signal, when illuminated with appropriate light source, that is significantly brighter than the signal from live cells. In one aspect the signal from dead cells is 10× brighter than the signal from live cells. In another aspect the signal from dead cells is 50× brighter than the signal from live cells. In yet another aspect the signal from dead cells is 100× brighter than the signal from live cells. See Example 37 and 38.

Thus, in one embodiment the present invention provides a method for evaluating the viability of cells in a sample, comprising
  a. combining a present compound with a sample to form a combined sample, wherein the compound comprises an amine reactive group;
  b. incubating the combined sample for a sufficient amount of time for the compound to form a covalent bond with amine groups on a cell membrane of live cells and to form covalent bonds with amine groups inside dead cells in the sample to form an incubated sample;

c. illuminating the incubated sample with an appropriate wavelength to form an illuminated sample; and
d. detecting the illuminated sample whereby the via of cells in a sample is evaluated.

In an alternative embodiment, dead cells are stained with a present compound and live cells stained with a know live cell stain wherein the two fluorescent signals can be distinguished from each other.

In another exemplary embodiment, the present invention provides a method for distinguishing between organisms expressing the same surface markers. Using coincidence staining, it is possible to identify differences in targets based on the ratio of surface marker expression. For example, despite intense efforts, no single binding-receptor has been found for the unambiguous detection of *B. anthracis* spores, due to extensive cross-reactivity with related *B. cereus* and *B. thuringiensis*, which are genetically a single species (Helgason et al., *Appl. Envir. Microbiol.* 66:2627-2630 (2000)). Despite being of the same species, however, the relative amount of various surface proteins is different between the three bacilli. Thus, multi-point detection of a variety of markers at the single cell level will provide the specificity required to detect *B. anthracis*.

Diagnostic tests that detect the presence or absence of a single marker are unable to distinguish among strains that are nearly identical at the genetic level, highlighting the need for new tools to distinguish between closely related organisms. Epidemics caused by emerging variants of known pathogens are a common theme in infectious diseases (Jiang et al., *Appl Environ Microbil* 66:148-53 (2000)) (Hedelberg et al. *Nature* 406:477-483 (2000)). There is also the problem of deliberate engineering of pathogens, incorporating virulence determinants from other species. An attack by such pathogens would be misdiagnosed due to the presence of markers not normally found in the attacking pathogen. By probing multiple markers within a single organism, using the methods of the invention, such variants are detected and preferably identified.

Detection by eye is also useful in those embodiments of the invention relying on coincidence staining. The human eye is extremely good at distinguishing between subtly different combinations of colors, especially when the colors are chosen correctly. By way of illustration, it is trivial for people to distinguish between the colors red, green and yellow. Yellow, however, is simply the spectral sum of red and green, so if red and green fluorescent conjugates are used for coincidence staining, positive assay signal can easily be identified by the perceived color, yellow. Other color combinations of use in this embodiment of the invention will be readily apparent to those of skill in the art, such as combinations of red, green and blue to form white.

Solutions of the compounds of the invention are prepared according to methods generally known in the art. As with related known fluorophores and fluorogens, the dyes and dye-conjugates are generally soluble in water and aqueous solutions having a pH greater than or equal to about 6. Stock solutions of pure dyes, however, are typically dissolved in organic solvent before diluting into aqueous solution or buffer. Preferred organic solvents are aprotic polar solvents such as DMSO, DMF, N-methylpyrrolidone, acetone, acetonitrile, dioxane, tetrahydrofuran and other nonhydroxylic, completely water-miscible solvents. In general, the amount of dye or conjugate in the dye solution is the minimum amount required to yield detectable staining in the sample within a reasonable time, with minimal background fluorescence or undesirable staining. The exact concentration of dye or dye-conjugate to be used is dependent upon the experimental conditions and the desired results, and optimization of experimental conditions is typically required to determine the best concentration of stain to be used in a given application. The concentration of dye present in the dye solution typically ranges from nanomolar to micromolar. The required concentration for the dye solution is determined by systematic variation in dye or dye-conjugate concentration until satisfactory dye staining is accomplished. The starting ranges are readily determined from methods known in the art for use of similar compounds under comparable conditions for the desired optical response.

The dye compounds are advantageously used to stain biological samples, i.e. samples that comprise biological components. In one embodiment of the invention, the sample comprises heterogeneous mixtures of components, including intact cells, cell extracts, bacteria, viruses, organelles, and mixtures thereof. In another aspect of the invention, the sample comprises a single component or homogeneous group of components, e.g. biological polymers such as amino acid polymers, nucleic acid polymers or carbohydrate polymers, or lipid membrane complexes, whether the polymers are synthetic or natural.

The sample is typically stained by passive means, i.e., by incubation with the dye solution. Any other method of introducing the dye into the sample, such as microinjection of a dye solution into a cell or organelle, can be used to accelerate introduction of the dye into the sample. The dyes of the present invention are generally non-toxic to living cells and other biological components, within the concentrations of use.

In one aspect of the invention, the sample is obtained directly from a liquid source or as a wash from a solid material (organic or inorganic) or a growth medium in which cells have been introduced for culturing, or a buffer solution in which cells have been placed for evaluation. In a further aspect, cells are isolated from biological fluids such as blood. Where the sample comprises cells, the cells are optionally single cells, including microorganisms, or multiple cells associated with other cells in two or three dimensional layers, including multicellular organisms, embryos, tissues, biopsies, filaments, biofilms, etc.

Alternatively, the sample is a solid, optionally a smear or scrape or a retentate removed from a liquid or vapor by filtration. In one aspect of the invention, the sample is obtained from a biological fluid, including separated or unfiltered biological fluids such as urine, cerebrospinal fluid, blood, lymph fluids, tissue homogenate, interstitial fluid, cell extracts, mucus, saliva, sputum, stool, physiological secretions or other similar fluids. Alternatively, the sample is obtained from an environmental source such as soil, water, or air; or from an industrial source such as taken from a waste stream, a water source, a supply line, or a production lot.

In yet another embodiment, the sample is present on or in solid or semi-solid matrix. In one aspect of the invention, the matrix is a membrane. In another aspect, the matrix is an electrophoretic gel, such as is used for separating and characterizing nucleic acids or proteins. In another aspect, the matrix is a silicon chip or glass slide, and the analyte of interest has been immobilized on the chip or slide in an array. In yet another aspect, the matrix is a microwell plate or microfluidic chip, and the sample is analyzed by automated methods, typically by various methods of high-throughput screening, such as drug screening.

The sample can be observed immediately after staining. A detectable optical response means a change in, or occurrence of, an optical signal that is detectable either by observation or instrumentally. Typically the detectable response is a change in fluorescence, such as a change in the intensity, excitation or emission wavelength distribution of fluorescence, fluorescence lifetime, fluorescence polarization, or a combination thereof. The degree and/or location of staining, compared with a standard or expected response, indicates whether and to what degree the sample possesses a given characteristic.

The sample is optionally combined with other solutions in the course of staining, including wash solutions, permeabilization and/or fixation solutions, and other solutions containing additional detection reagents. Washing following staining generally improves the detection of the optical response due to the decrease in non-specific background fluorescence after washing. Satisfactory visualization is possible without washing by using lower labeling concentrations. A number of fixatives and fixation conditions suitable for practicing this invention are known in the art, including formaldehyde, paraformaldehyde, formalin, glutaraldehyde, cold methanol and 3:1 methanol:acetic acid. Fixation is typically used to preserve cellular morphology and to reduce biohazards when working with pathogenic samples. Selected embodiments of the dyes described above are well retained in cells, and sample cells stained with these dyes retain considerable fluorescent staining after fixation. Fixation is optionally followed or accompanied by permeabilization, such as with acetone, ethanol, DMSO or various detergents, to allow bulky dye compounds, including dye-conjugates described above, to cross cell membranes, according to methods generally known in the art. The staining of the present invention is optionally combined with the use of an additional detection reagent that produces a detectable response due to the presence of a specific cell component, intracellular substance, or cellular condition, according to methods generally known in the art. Where the additional detection reagent has spectral properties that differ from those of the subject dye compounds, multicolor applications are possible. The compounds of the invention are also of use to derivative low molecular weight compounds for their analysis by capillary zone electrophoresis (CZE), HPLC or other separation techniques.

Sample Preparation

The end user will determine the choice of the sample and the way in which the sample is prepared. The sample includes, without limitation, any biological derived material or aqueous solution that is believed to contain a target analyte or ligand. Alternatively, samples also include material in which an analyte or ligand has been added.

The sample can be a biological fluid such as whole blood, plasma, serum, nasal secretions, sputum, saliva, urine, sweat, transdermal exudates, cerebrospinal fluid, or the like. Biological fluids also include tissue and cell culture medium wherein an analyte of interest has been secreted into the medium. Alternatively, the sample may be whole organs, tissue or cells from the animal. Examples of sources of such samples include muscle, eye, skin, gonads, lymph nodes, heart, brain, lung, liver, kidney, spleen, thymus, pancreas, solid tumors, macrophages, mammary glands, mesothelium, and the like. Cells include without limitation prokaryotic cells and eukaryotic cells that include primary cultures and immortalized cell lines. Eukaryotic cells include without limitation ovary cells, epithelial cells, circulating immune cells, 3 cells, hepatocytes, and neurons.

One may use an individual compound of the invention, multiple compounds of the invention or a combination of a compound of the invention and a fluorophore or quencher of a different structure in order to detect the presence of or determine the characteristics of a target in a sample.

When the components of the invention are species that bind to targets that are specific biological structures (e.g., enzymes, receptors, ligands, antigens, antibodies, etc.), the reaction time between the compound or conjugate of the invention and the target will usually be at least about 5 min, more usually at least about 30 min and preferably not more than about 180 min, preferably not more than about 120 min, depending upon the temperature, concentrations of enzyme and substrate, etc. By using a specific time period for the reaction or taking aliquots at 2 different times, the rate of reaction can be determined for comparison with other determinations. The temperature will generally be in the range of about 20 to 50° C., more usually in the range of about 25 to 40° C.

Various buffers can be used in the assays of the invention. These buffers include PBS, Tris, MOPS, HEPES, phosphate, etc. The pH will vary depending upon the particular assay system, generally within a readily determinable range wherein one or more of the sulfonic acid moieties is deprotonated. The concentration of buffer is generally in the range of about 0.1 to 50 mM, more usually 0.5 to 20 mM.

In many instances, it may be advantageous to add a small amount of a non-ionic detergent to the sample. Generally the detergent will be present in from about 0.01 to 0.1 vol. %. Illustrative non-ionic detergents include the polyoxyalkylene diols, e.g. Pluronics, Tweens, Triton X-100, etc.

In fluorescence experiments, the reaction is optionally quenched. Various quenching agents may be used, both physical and chemical. Conveniently, a small amount of a water-soluble solvent may be added, such as acetonitrile, DMSO, SDS, methanol, DMF, etc.

Illumination

The compounds of the invention may, at any time after or during an assay, be illuminated with a wavelength of light that results in a detectable optical response, and observed with a means for detecting the optical response. Upon illumination, such as by an violet or visible wavelength emission lamp, an arc lamp, a laser, or even sunlight or ordinary room light, the fluorescent compounds, including those bound to the complementary specific binding pair member, display intense visible absorption as well as fluorescence emission. Selected equipment that is useful for illuminating the fluorescent compounds of the invention includes, but is not limited to, handheld ultraviolet lamps, mercury arc lamps, xenon lamps, argon lasers, laser diodes, and YAG lasers. These illumination sources are optionally integrated into laser scanners, flow cytometer, fluorescence microplate readers, standard or mini fluorometers, or chromatographic detectors. This fluorescence emission is optionally detected by visual inspection, or by use of any of the following devices: CCD cameras, video cameras, photographic film, laser scanning devices, fluorometers, photodiodes, quantum counters, epifluorescence microscopes, scanning microscopes, flow cytometers, fluorescence microplate readers, or by means for amplifying the signal such as photomultiplier tubes. Where the sample is examined using a flow cytometer, a fluorescence microscope or a fluorometer, the instrument is optionally used to distinguish and discriminate between the fluorescent compounds of the invention and a second fluorophore with detectably different optical properties, typically by distinguishing the fluorescence response of the fluorescent compounds of the invention from that of the second fluorophore. Where a sample is examined using a flow cytometer, examination of the sample optionally includes isolation of particles within the sample based on the fluorescence response by using a sorting device.

Kits of the Invention

In another aspect, the present invention provides kits that include a fluorescent compound of the invention. The kit will generally also include instructions for using the compound of the invention in one or more methods.

In an exemplary embodiment, the kit includes a reactive compound of the invention and instructions for conjugating the dye to any substance possessing an appropriate functional group, and optionally for recovering or purifying the materials labeled thereby. This combination of reactive dye and instructions therefore comprise a kit for labeling an appropriate substance. Selected appropriate substances include, but are not limited to, polymers of biological molecules (e.g. proteins, oligonucleotides or carbohydrates), polymeric resins and plastics (e.g. polystyrene), metals, glasses, and other organic or inorganic substances. The dyes of the present invention are well-suited for the preparation of such a kit.

In another exemplary kit of the invention, the instructions provided are for performing an assay that detects an analyte or ligand in a sample. Typically the kit would comprise a dye conjugated to a secondary antibody. In this way the end user would provide the primary antibody resulting in an unlimited number of ligand or analytes that could be detected. Alternatively the kit would comprise the dye-labeled secondary and a primary antibody. For example, in one embodiment, directions are provided for detecting a cell receptors, or an enzyme, organism, or other ligands that are bound by antibodies.

A detailed description of the invention having been provided above, the following examples are given for the purpose of illustrating the invention and shall not be construed as being a limitation on the scope of the invention or claims.

A detailed description of the invention having been provided above, the following examples are given for the purpose of illustrating the invention and shall not be construed as being a limitation on the scope of the invention or claims.

EXAMPLES

Example 1

Synthesis of Compound 1

A mixture of 3.6 g of 4-hydroxyacetophenone, 5.7 g of methyl 5-bromovalerate, and 8.1 g of $K_2CO_3$ in 50 mL of DMF was heated at 75° C. overnight. After the reaction mixture was cooled to room temperature, it was extracted with ethyl acetate, washed with water, and dried over anhydrous $Na_2SO_4$ to obtain product Compound 1.

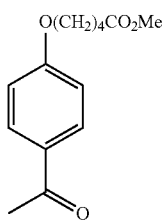

Compound 1

Example 2

Synthesis of Compound 2

To 7.0 g of Compound 1 in 60 mL of $CHCl_3$, 4.3 g of bromine (in 10 mL of $CHCl_3$) was added slowly at room temperature and stirred for an additional 3 h. All volatile components were removed under reduced pressure and the residue was purified on a silica gel column with ethyl acetate and hexanes.

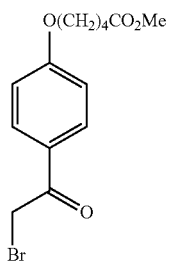

Compound 2

Example 3

Synthesis of Compound 3

To 6.0 g of Compound 2 in 30 mL of $CHCl_3$ at 0° C., 3.1 g of metheamine (in 50 mL of $CHCl_3$) was added slowly at room temperature and stirred for another 4 h. All volatile components were removed under reduced pressure to give the product Compound 3.

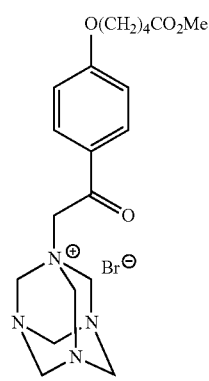

Compound 3

Example 4

Synthesis of Compound 4

To 9.2 g of Compound 3 suspended in 150 mL of ethanol at 0° C., 12 mL of concentrated HCl was added slowly and the mixture was stirred at 40° C. for 4 h. All volatile components were then removed under reduced pressure to recover product Compound 4.

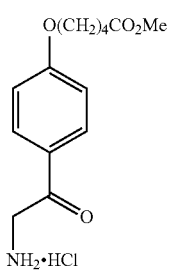

Compound 4

Example 5

Synthesis of Compound 5

To 9.0 g of Compound 4 in 150 mL of CHCl₃ at 0° C., 12 g of triethylamine was introduced followed by a solution of iso-nicotinoylchloride hydrochloride (6.4 g in a mixture of 50 mL of CHCl₃ and 50 mL of DMF). The mixture was warmed to room temperature and stirred at room temperature overnight. The reaction mixture was then poured into water and extracted with CHCl₃. The organic layer was washed with saturated aqueous Na₂CO₃ and water and the crude product was purified on a silica gel column with MeOH and CHCl₃.

Compound 5

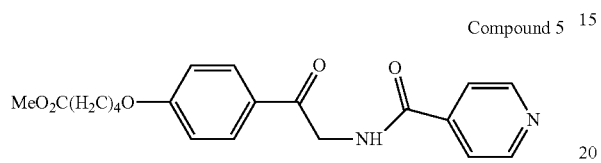

Example 6

Synthesis of Compound 6

A mixture of 2.0 g of Compound 5 and 25 mL of phosphorous oxychloride was heated at reflux temperature for 10 h. After the reaction mixture was cooled to room temperature, excess phosphorous oxychloride was removed by rotary evaporation and the residue was dissolved in 100 mL of ethyl acetate and washed with saturated aqueous Na₂CO₃, water and dried over anhydrous Na₂SO₄. The solvent was removed to give 1.9 g of product Compound 6.

Compound 6

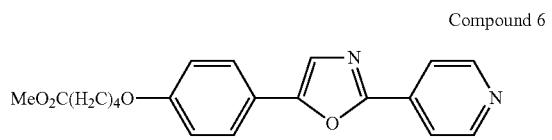

Example 7

Synthesis of Compound 7

A mixture of compound 1.9 g of Compound 6 and 8.0 g of propane sultone in 30 mL of acetonitrile was heated at 110° C. for 2 h. After cooling to about 50° C., an ethyl acetate/hexanes mixture (150 mL, 1:1, v/v) was added and product Compound 7 was collected by filtration.

Compound 7

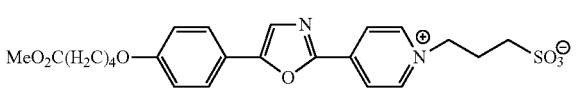

Example 8

Synthesis of Compound 8

A solution of 3.6 g of Compound 7 in 150 mL of concentrated HCl and 100 mL of water was heated at 65° C. for 2 days and all volatile components were removed under reduced pressure to give the crude carboxylic acid. The crude acid was dissolved in 15 mL concentrated H₂SO₄ and after cooled to 0° C., 15 mL of 30% fuming H₂SO₄ was added and the mixture was stirred at the low temperature for 1 h. The reaction mixture was poured into 500 mL of cold Et₂O and the crude product was collected by filtration and further purified by HPLC to give 1.6 g of pure product Compound 8.

Compound 8

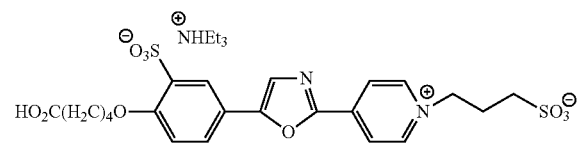

Example 9

Synthesis of Compound 9A

To 1.6 g of Compound 8 in 500 mL of anhydrous DMA (500 mL), 1.6 g of N,N'-disuccinimidyl carbonate and 62 mg of N,N-dimethylaminopyridine were added and the reaction mixture was stirred at room temperature as a suspension for 2 days. At the end of the period, the volume of the reaction mixture was reduced to ~100 mL under reduced pressure and 300 mL of ethyl acetate was added and stirred for V2 h. The solid was collected by filtration and washed with ethyl acetate to give 1.7 g of product Compound 9A.

Compound 9A

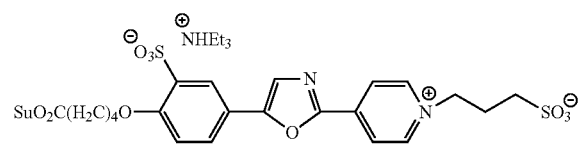

Example 10

Synthesis of Compound 9B

To 100 mg of Compound 9A in 10 mL of anhydrous dimethylacetamide at 0° C., 100 mg of hydrazine was added and the reaction mixture was stirred at 0° C. for 1 h. The solvent was removed under vacuum and the residue was purified by HPLC to give product Compound 9B Compound 9B

Example 11

Synthesis of Compound 9C

To 100 mg of Compound 9A in 10 mL of anhydrous dimethylacetamide at 0° C., 90 mg of N-(2-aminoethyl)maleimide trifluoroacetic acid salt and 0.1 mL of triethyl amine were added and the reaction mixture was stirred at 0° C. for 1 h. The solvent was removed under vacuum the residue was purified by HPLC to give product Compound 9C.

Compound 9C

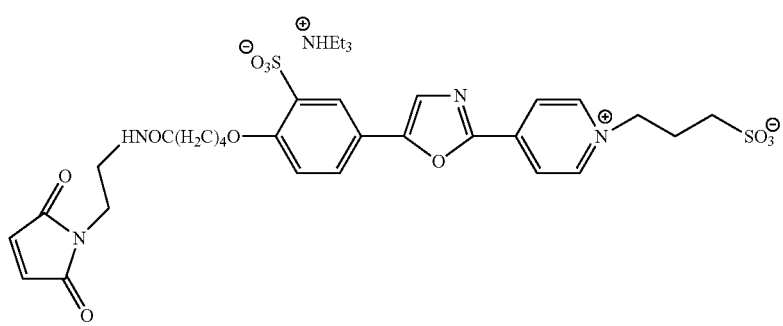

Example 12

Synthesis of Compound 10

Compound 10 was prepared by following the same procedure for compound 1 with 4-hydroxyphenylacetone as the starting material.

Compound 10

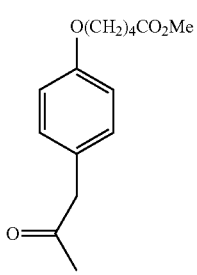

Example 13

Synthesis of Compound 11

A mixture of 2.5 g of Compound 10, 0.72 g of hydroxylamine hydrochloride, 1.8 g of diisopropylethylamine in 50 mL of EtOH was heated at 75° C. for 20 minutes. The solvent was removed and the residue was dissolved in 200 mL of ethyl acetate and washed with 1% HCl, and dried over anhydrous $Na_2SO_4$ to give the product Compound 11.

Compound 11

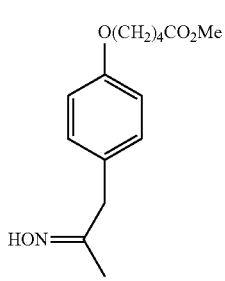

Example 14

Synthesis of Compound 12

A mixture of 1.9 g of Compound 11 and 1.8 g of isonicotinoylchloride hydrochloride in 30 mL of pyridine was heated the at 95° C. overnight. The solvent was removed and the residue was partitioned between ethyl acetate and saturated sodium carbonate and the organic layer was dried over anhydrous $Na_2SO_4$. The crude product is purified on a silica gel column with MeOH and $CHCl_3$.

Compound 12

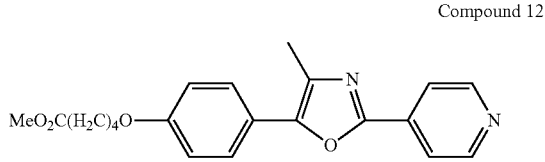

Example 15

Synthesis of Compound 13

Compound 13 was prepared from Compound 12 by following the same procedures for the transformation of Compound 6 to compound 9A.

Compound 13

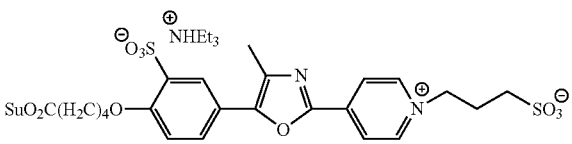

Example 16

Synthesis of Compound 14

A mixture of 300 mg of 2-amino-4'-methoxyacetonphenone hydrochloride and 270 mg of 4-quinolinecarboxylic acid in 5 mL of phosphorous oxychloride was refluxed for 5 h and after cooling to room temperature, excess phosphorous oxychloride was evaporated under reduced pressure. The residue was partitioned ethyl acetate and saturated sodium carbonate and the organic layer was then washed with water and dried over anhydrous $Na_2SO_4$. The crude product is purified on a silica gel column with $CHCl_3$ and ethyl acetate.

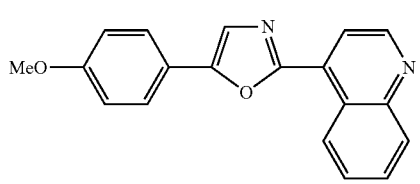

Compound 14

Example 17

Synthesis of Compound 15

Compound 15 was prepared by following the same procedures for compound 8 using compound 14 as starting material.

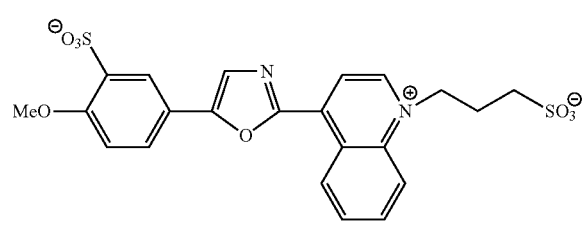

Compound 15

Example 18

Synthesis of Compound 16

Compound 16 was prepared from 4-chloroacetyl-1-methoxynaphthalene by following the aforementioned procedures.

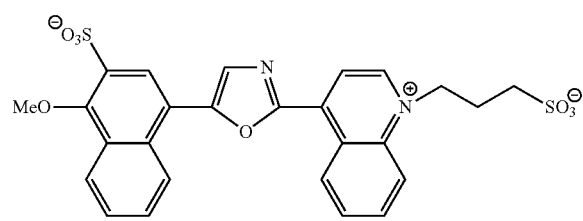

Compound 16

Example 19

Synthesis of Compound 17

Compound 17 was prepared from 2,4-dimethoxyacetophenone and 6-methoxy-2-phenyl-4-quinolinecarboxylic acid by following the aforementioned procedures.

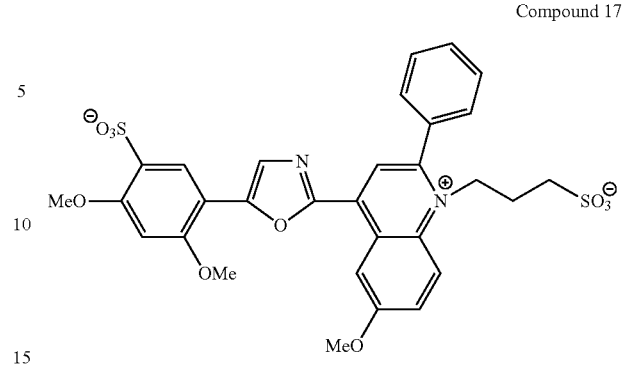

Compound 17

Example 20

Synthesis of Compound 18

Compound 18 was prepared from 2,4-dimethoxyacetophenone and 4-quinolinecarboxylic acid by following the aforementioned procedures.

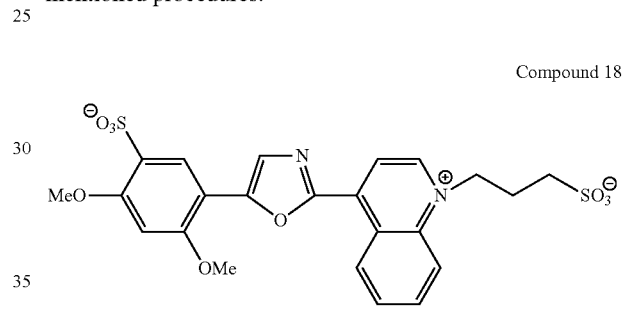

Compound 18

Example 21

Synthesis of Compound 19

Compound 19 was prepared from 3,4-dimethoxyacetophenone and 4-quinolinecarboxylic acid by following the aforementioned procedures.

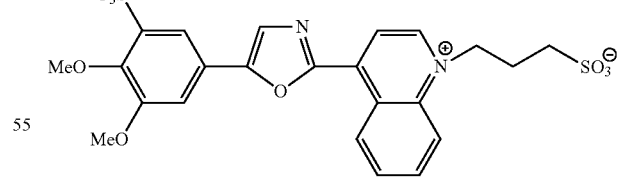

Compound 19

Example 22

Synthesis of Compound 20

A mixture of 2.5 g of 6'-methoxy-2'-acetonaphthone and 5.6 g of copper (II) bromide in 100 mL of CHCl$_3$/ethyl acetate (1:1 v/v) was heated at reflux temperature for 3 h. After the reaction mixture was cooled to room temperature, the precipitate was filtered off and washed with CHCl₃. The crude product was recrystallized from CHCl₃ and hexanes.

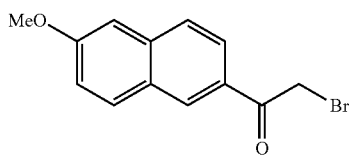
Compound 20

Example 23

Synthesis of Compound 21

To 0.7 g of compound 20 in 50 mL of CHCl₃ at 0° C., 0.44 g of metheamine was added slowly at room temperature and stirred overnight. At the end of the period 100 mL of hexane was added to the reaction mixture and the precipitate was collected to give the product Compound 21 (1.0 g).

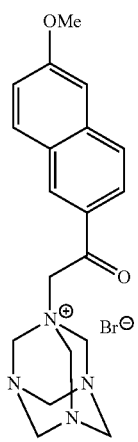
Compound 21

Example 24

Synthesis of Compound 22

To 0.65 g of Compound 21 suspended in 30 mL of ethanol at 0° C., 5 mL of concentrated HCl was added slowly and the mixture was stirred at 40° C. for 4 h. All volatile components were then removed under reduced pressure to recover product Compound 22.

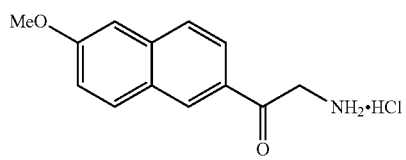
Compound 22

Example 25

Synthesis of Compound 23

A mixture of 100 mg of Compound 22 and 150 mg of 4-quinolinecarboxylic acid in 5 mL of phosphorous oxychloride was refluxed for 10 h and after cooling to room temperature, excess phosphorous oxychloride was evaporated under reduced pressure. The residue was partitioned with ethyl acetate and saturated sodium carbonate and the organic layer was then washed with water and dried over anhydrous Na₂SO₄. The crude product is purified on a silica gel column with CHCl₃ and ethyl acetate.

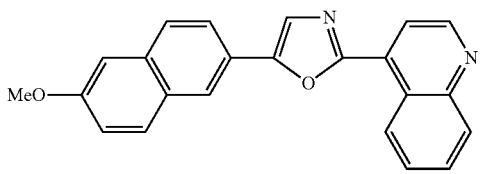
Compound 23

Example 26

Synthesis of Compounds 24A and 24B

Compounds 24A and 24B were prepared from Compound 23 by first reacting with propane sultone followed by sulfonation with fuming sulfuric acid according to the aforementioned procedures.

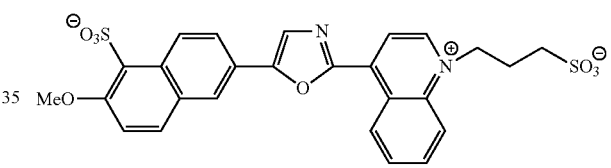
Compound 24A

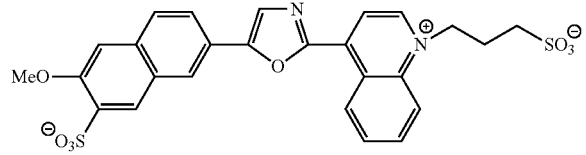
Compound 24B

TABLE 3

Spectral properties of selected compounds of the invention in PBS buffer (pH = 7.0)

| Compound | Absorbance maximum (nm) | Emission maximum (nm) |
|---|---|---|
| Compound 8 | 396 | 549 |
| Compound 13 | 404 | 550 |
| Compound 15 | 428 | 597 |
| Compound 18 | 451 | 632 |
| Compound 19 | 401 | 462 |

Example 27

Synthesis of Compounds 25-31

To a mixture of 4-hydroxyphenylboronic acid (1.38 g), 2,5-dibromothiophene (4.84 g), tetrakis(triphenylphosphine) palladium (0) (1.24 g), toluene (60 mL) and iso-propyl alcohol (30 mL), 4.14 g of $K_2CO_3$ (in 10 mL of water) was added. $N_2$ was bubbled through the mixture for several minutes and the resulting suspension was heated at 100° C. under $N_2$ with vigorous stirring for 5 h. After cooling to room temperature and diluting with water, the resulting mixture was acidified to pH 2 with 4% HCl and extracted with EtOAc. The organic layer was washed with water and dried over anhydrous $Na_2SO_4$. The residue was purified on a silica gel column with hexanes and EtOAc to give 1.2 g of 25.

Compound 25

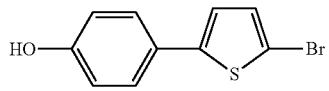

Compound 25 (1.2 g) was heated in 30 mL of DMF with methyl 5-bromovalerate (1.38 g) and $K_2CO_3$ (1.95 g) at 75° C. for 4 h. The mixture was cooled to room temperature, diluted with water and extracted with EtOAc. The crude was purified on a silica gel column with hexanes and EtOAc to give 1.25 g of 26.

Compound 26

To a mixture of compound 26 (1.05 g), 4-pyridineboronic acid (0.53 g), tetrakis(triphenylphosphine)palladium (0) (0.35 g), toluene (30 mL) and iso-propyl alcohol (15 mL), 1.2 g of $K_2CO_3$ (in 5 mL of water) was added. The suspension was purged with $N_2$ and heated at 100° C. under $N_2$ for 2 h. The reaction mixture was cooled to room temperature, diluted with water and extracted with EtOAc. The crude was purified on a silica gel column with $CHCl_3$ and MeOH to give 0.81 g of 27.

Compound 27

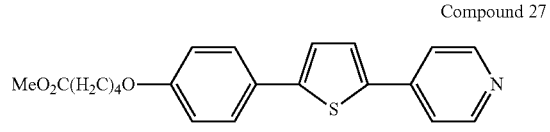

A mixture of compound 27 (0.52 g) and 1,3-propane sultone (4.0 g) was refluxed in 10 mL of $CH_3CN$ for 10 h. After the mixture was cooled to about 50° C., 150 mL of a 1/1 mixture (v/v) of EtOAc/hexanes was added, and product 28 was collected by filtration.

Compound 28

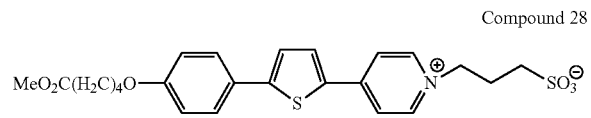

Compound 28 (0.36 g) was hydrolyzed with aqueous HCl (con. HCl/water, 60 mL/20 mL) at 65° C. for 3 days. All volatile components were removed in vacuo to obtain 29. The crude compound 29 thus obtained was dissolved in conc. $H_2SO_4$ (10 mL), cooled to 0° C. before 5 mL of 30% fuming $H_2SO_4$ was introduced slowly and the resulting mixture was stirred at 0° C. for 1 h. The reaction mixture was then poured into 300 mL of cold $Et_2O$, and the crude was collected by filtration and purified on HPLC to give 0.15 g of 30.

Compound 29

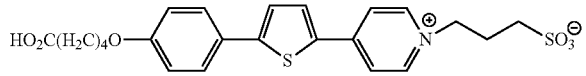

Compound 30

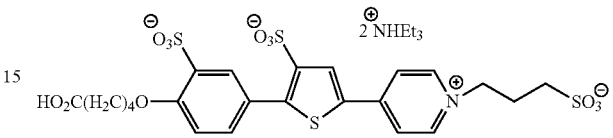

To compound 30 (50 mg) in 10 mL of anhydrous dimethylacetamide, 40 mg of N,N'-disuccinimidyl carbonate and 3 mg of 4-dimethylaminopyridine were added and the resulting mixture was stirred at room temperature for 3 h. At the end of the period, 100 mL of EtOAc was added and after stirring for an additional 0.5 h, the solid was filtered, washed with EtOAc and dried in vacuo to give 50 mg of product 31.

Compound 31

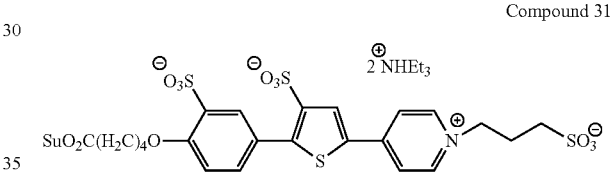

Example 28

Synthesis of Compounds 32-34

To 2-amino-4'-methoxyacetonphenone hydrochloride (0.5 g) in 30 mL of anhydrous dimethylacetamide at 0° C., triethylamine (3.0 mL) was added and followed by iso-nicotinoylchloride hydrochloride (0.52 g). The mixture was then warmed to room temperature and stirred for an additional 3 h. The reaction was diluted with water, extracted with EtOAc and dried over anhydrous $Na_2SO_4$. Crude yield was 0.63 g of Compound 32.

Compound 32

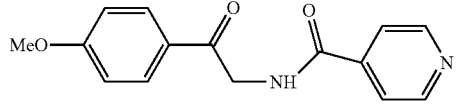

A mixture of crude 32 (0.63 g) and Lawesson's reagent (2.4 g) was refluxed in 80 mL of anhydrous THF under $N_2$ for 8 h. The volatile components were removed under reduced pressure and the crude was purified on a silica gel column with $CHCl_3$ and MeOH to give 0.75 g of 33.

Compound 33

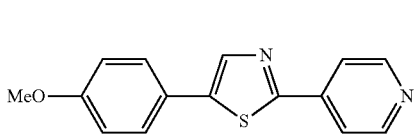

A mixture of compound 33 (0.70 g) and 1,3-propane sultone (3.0 g) was refluxed in 10 mL of CH₃CN for 10 h. The mixture was cooled to ~50° C. and 150 mL of a 1:1 (v/v) mixture of EtOAc/hexanes was added and the product, Compound 34, was collected by filtration.

Compound 34

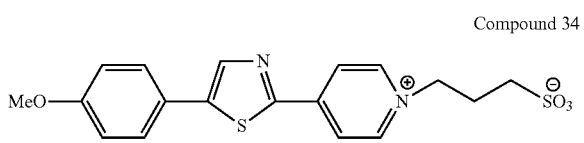

Example 29

Synthesis of Compound 35

Compound 35 was prepared by following the same procedure for compound 30 starting with compound 34.

Compound 35

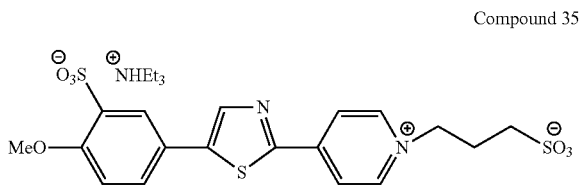

Example 30

Synthesis of Compound 36

To N-[2-keto-2-(4-pyridyl)ethyl]-4-methoxybenzamide (0.50 g) in a flask, POCl₃ (10 mL) was added and refluxed for 1 h. The reaction mixture was cooled to room temperature and all volatiles were removed under reduced pressure and the residue was dissolved in EtOAc, and washed with saturated aqueous Na₂CO₃. The crude thus obtained was purified on a silica gel column with CHCl₃ and MeOH to give 0.3 g of 36.

Compound 36

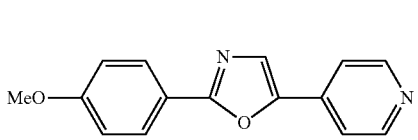

Example 31

Synthesis of Compound 37

Compound 37 was prepared by following the same procedure for compound 35 starting from compound 36.

Compound 37

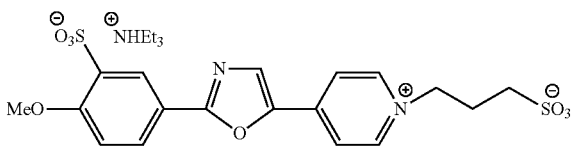

Example 32

Two Color Immunophenotyping Using Pacific Blue Dye and Compound 9

Human mononuclear cells were harvested from CPT (Ficol) tubes (BD Bioscience). Cells were washed with 1% BSA/PBS and resuspended at a concentration of 10 million/mL. A mouse anti-human CD4 primary antibody (BD Pharmingen) was labeled with the Zenon Pacific Blue™ Labeling Kit. The cells were then stained with Zenon Pacific Blue mouse anti-human CD4 complex and 1 microgram of mouse anti-human CD8 Compound 9 for 30 minutes. The cells were washed with 1% BSA/PBS, centrifuged, and resuspended with 400 microliters of 1% BSA/PBS. The samples were analyzed on a LSR II flow cytometer exiting with a 405 nm diode laser, collecting emission with 450/50 nm and 575/26 emission filters. Using a forward scatter vs. side scatter dot plot the lymphocytes were gated and plots were made using a lymphocyte gate. Compensation was applied using single color controls. See, FIG. 1.

Example 33

Conjugation of Compound 9A Succinimidyl Ester (SE) and goat anti-mouse IgG (GAM) 0.221 mL (1.5 mg) of a 6.8 mg/mL solution of GAM in 10 mM potassium phosphate, 150 mM sodium chloride buffer (PBS) was measured into test tubes and the pH raised to >8.0 with 22 μL 1 M sodium bicarbonate, pH 9.0. The GAM solution was reacted with a 10, 20, 30, 40, or 50-fold molar excess of the Compound 9 at 20 mg/mL in anhydrous DMSO for 1 h at RT. The dye-protein conjugates were separated from free dye by size exclusion chromatography using 5-0.75×20 cm columns packed with BioRad™ Bio-Gel® P-30 fine in PBS and eluted with same. The initial protein-containing band from each column was collected.

Absorbance spectra were obtained on a Perkin-Elmer Lambda 35 UVN is spectrometer. The fluorescence emission spectra were obtained using an Aminco Bowman Series 2 Luminescence Spectrometer, excited at 390 nm. Cell staining of the GAM-Compound 9A conjugates was performed using INOVA Diagnostics, Inc. prefixed HEp-2 cells in a 12 wells/slide format to detect mouse anti-human IgG antibody labeling of human anti-nuclear antibodies. Samples were prepared in 1% bovine serum albumin in PBS at 1 μg/mL and 10 pg/mL and let incubate 30 min at RT in both positive and control wells. Wells were washed 4× with PBS, soaking for 10 minutes in PBS prior to wet mounting in PBS with a coverslip. The cells were imaged using filter sets from Omega® Optical, XF12 in a Nikon Eclipse E400 fluorescence microscope and Princeton Instruments, Inc. RTE/CCD-728-Y camera using MetaMorph Imaging System from Universal Imaging Corporation.

Example 34

Conjugation of Compound 9A Succinimidyl Ester (SE) and streptavidin (SA) 0.1 mL (1 mg) of a 10.0 mg/mL solution of SA in 0.1M sodium bicarbonate was reacted with a 5, 10, 20, 30, 40, or 80-fold molar excess of the Compound 9A at 20 mg/mL in anhydrous DMSO for 1 h at RT. The dye-protein conjugates were separated from free dye by size exclusion chromatography using 6-0.75×20 cm columns packed with BioRad™ Bio-Gel® P-30 fine in PBS and eluted with same. The initial protein-containing band from each column was collected.

Absorbance spectra were obtained on a Perkin-Elmer Lambda 35 UV/Vis spectrometer. The fluorescence emission spectra were obtained using an Aminco Bowman Series 2 Luminescence Spectrometer, excited at 390 nm. Cell staining of the SA-Compound 9A conjugates was performed using INOVA Diagnostics, Inc. prefixed HEp-2 cells in a 12 wells/slide format to detect biotinylated goat anti-human IgG antibody labeling of human anti-nuclear antibodies. Samples were prepared in 1% bovine serum albumin in PBS at 10 μg/mL and let incubate 30 min at RT in both positive and control wells. Wells were washed 4× with PBS, soaking for 10 minutes in PBS prior to wet mounting in PBS with a coverslip. The cells were imaged using filter sets from Omega® Optical, XF12 in a Nikon Eclipse E400 fluorescence microscope and Princeton Instruments, Inc. RTE/CCD-728-Y camera using MetaMorph Imaging System from Universal Imaging Corporation.

Example 35

Comparison of Cascade Yellow and Compound 9A Conjugates

Mononuclear cells were harvested from CPT Ficoll tubes. Cells were counted and resuspended at $1 \times 10^7$/mL. 1004 of cells were aliquoted to test tubes. Cells were blocked with 10 μL mouse IgG, incubated with appropriate primary antibody mouse anti-human CD4 biotin, RT/dark, 30 min, cells were washed with 1% BSA/PBS, incubated with streptavidin conjugates at concentrations ranging from 1 μg-0.008 μg. Cells were washed and resuspended in 1% BSA/PBS and analyzed on LSR II using blue/red/violet/and UV excitation.

Figure 3:
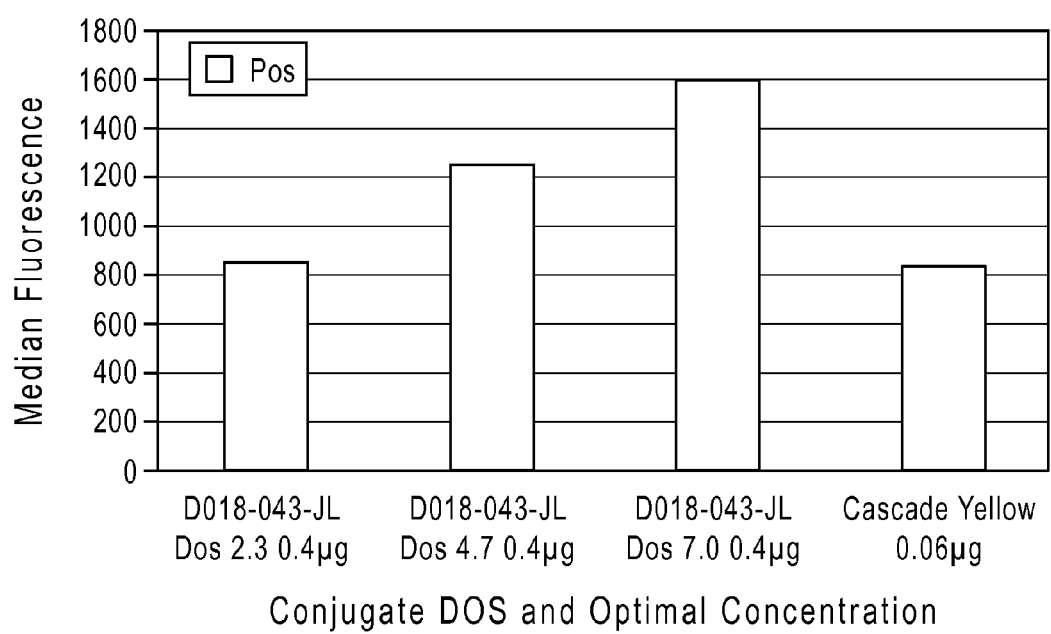
FIG. 3: Shows comparison of Cascade Yellow to Compound 9A with 3 different DOL.
Figure 4A:
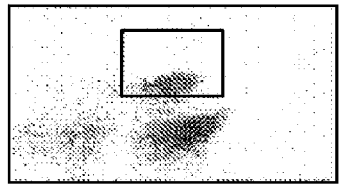
FIG. 4: Shows the brighter signal of Compound 9A mouse anti-human CD8 compared to AmCyan mouse anti-human CD8 and CD4.
Figure 4B:
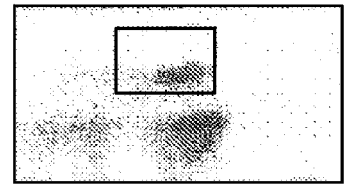
Figure 4C:
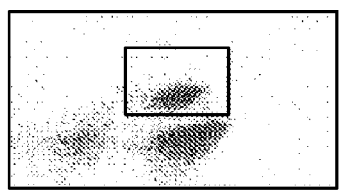
Figure 4D:
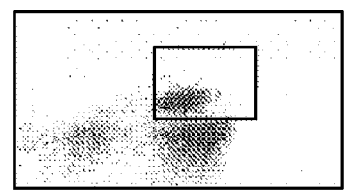
Figure 4E:
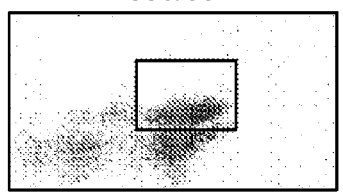
Figure 4F:
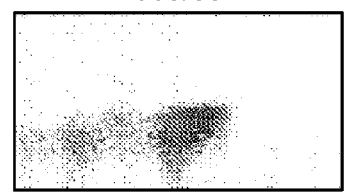
Figure 4G:
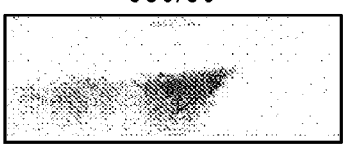
Figure 4H:
Figure 5A:
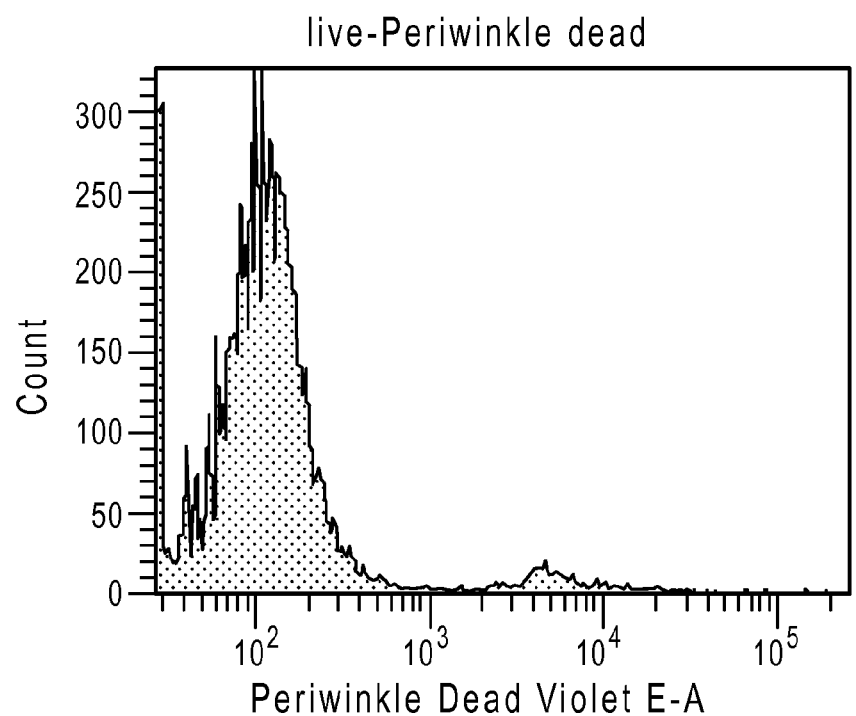
FIG. 5: Shows histograms for cells stained with the Compound 31; a) live cells show low fluorescence b) aged culture cells, c) ethanol-killed cells, and d) heat-killed cells all show higher fluorescence than live cells.
Figure 5B:
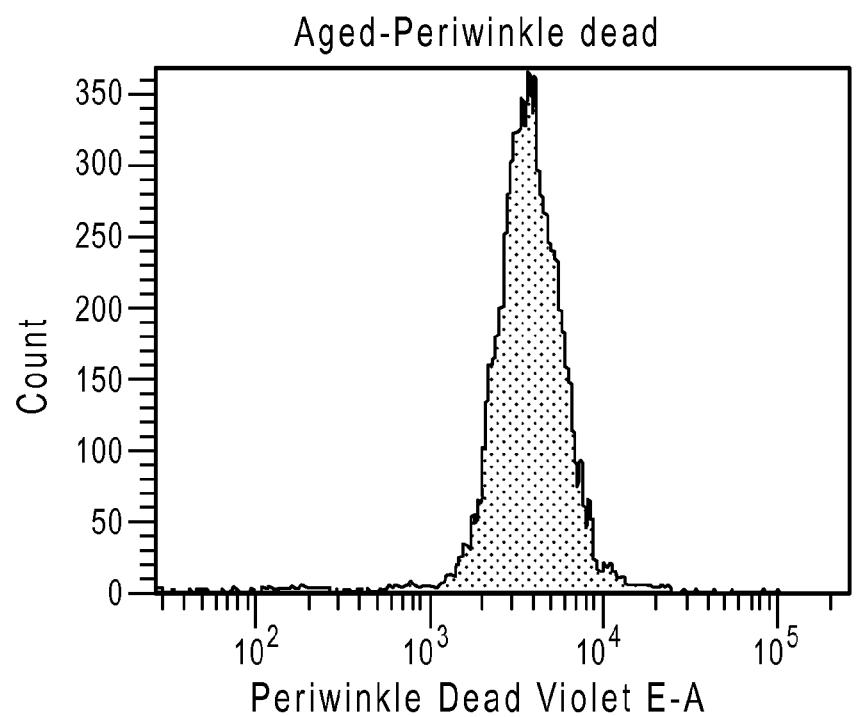
Figure 5C:
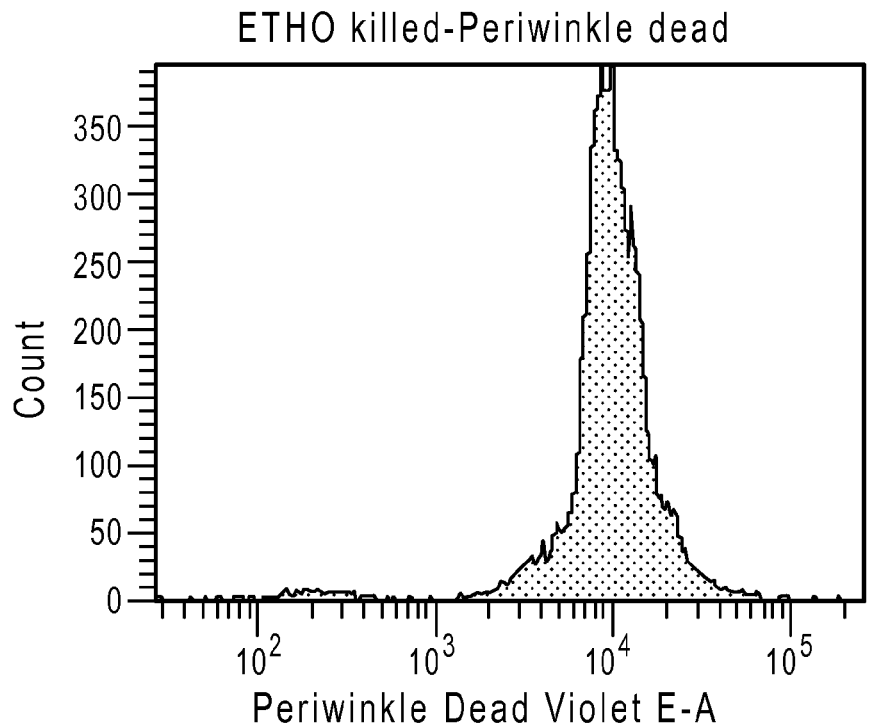
Figure 5D:
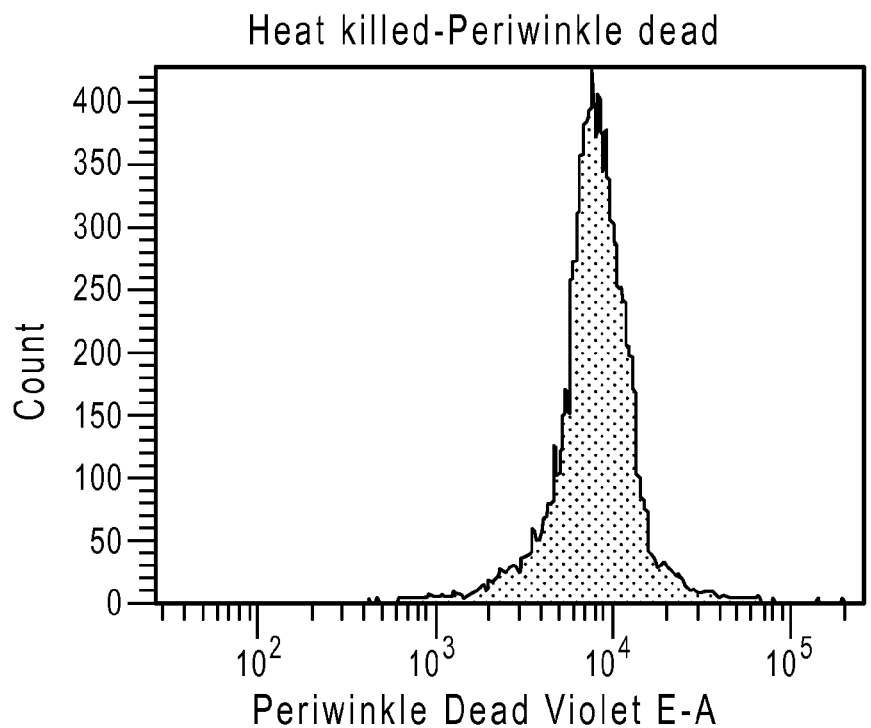
Figure 6A:
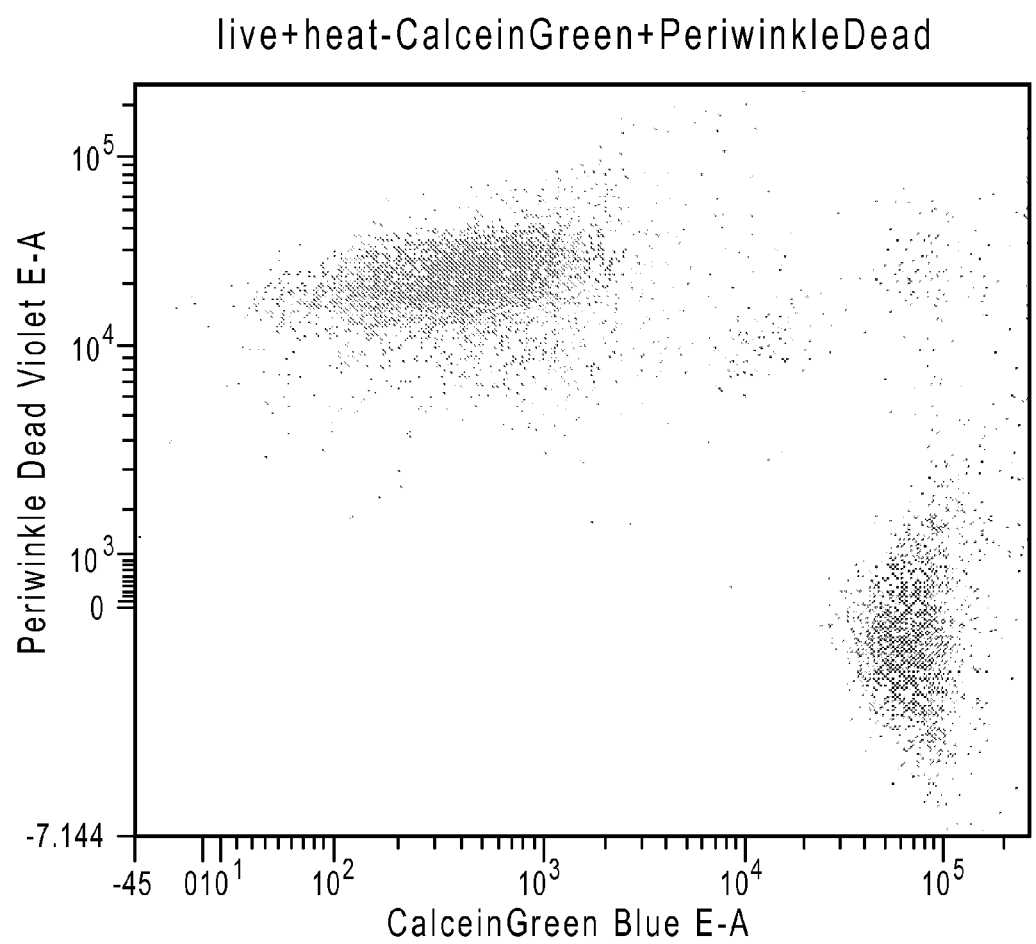
FIG. 6: Shows dual parameter dot plots demonstrating Compound 31 satin with two calcein AM live cell stains. a) Mixture of live and heat-killed Jurkat cells stained with calcein green, AM and Compound 31, showing two distinct populations. b) Mixture of live and ethanol-killed jurkat cells stained with calcein green, AM and Compound 31, showing two distinct populations. c) Mixture of live and heat-killed Jurkat cells stained with calcein violet, AM and Periwinkle dead stain, showing two distinct populations. d) Mixture of live and ethanol-killed jurkat cells stained with calcein violet, AM and Compound 31, showing two distinct populations.
Figure 6B:
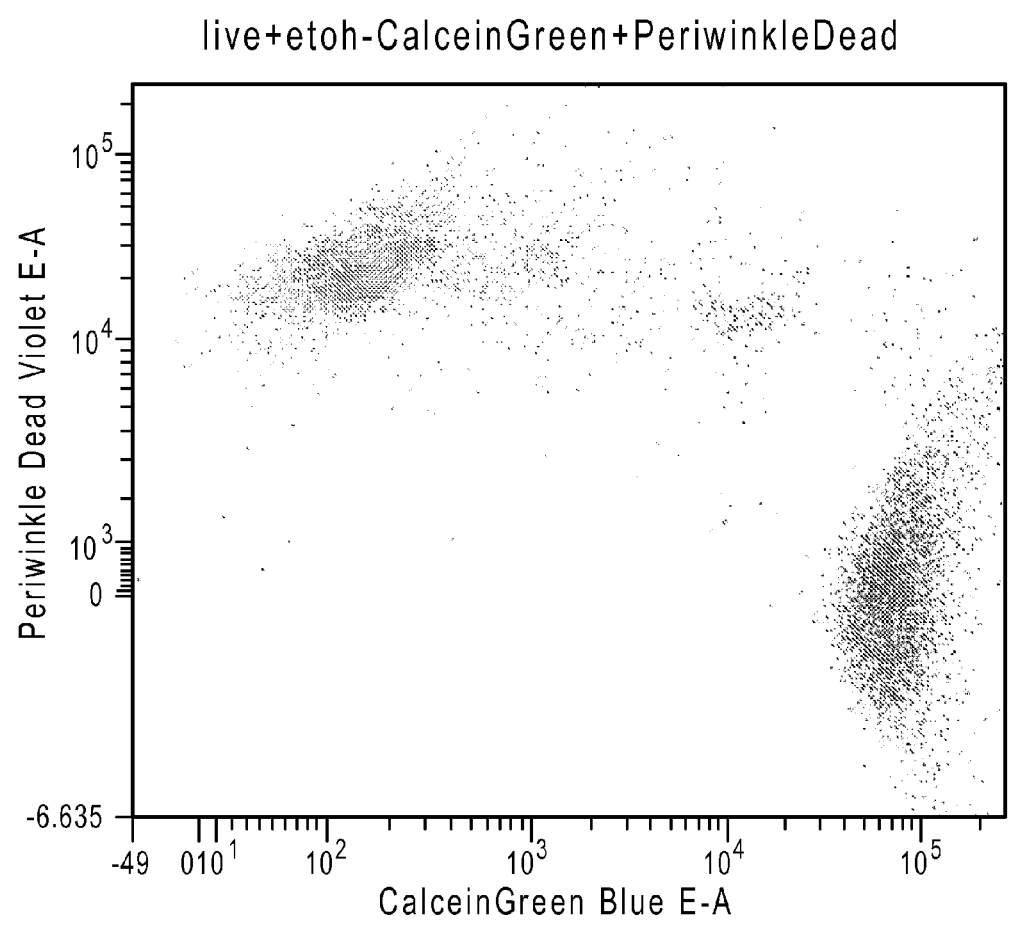
Figure 6C:
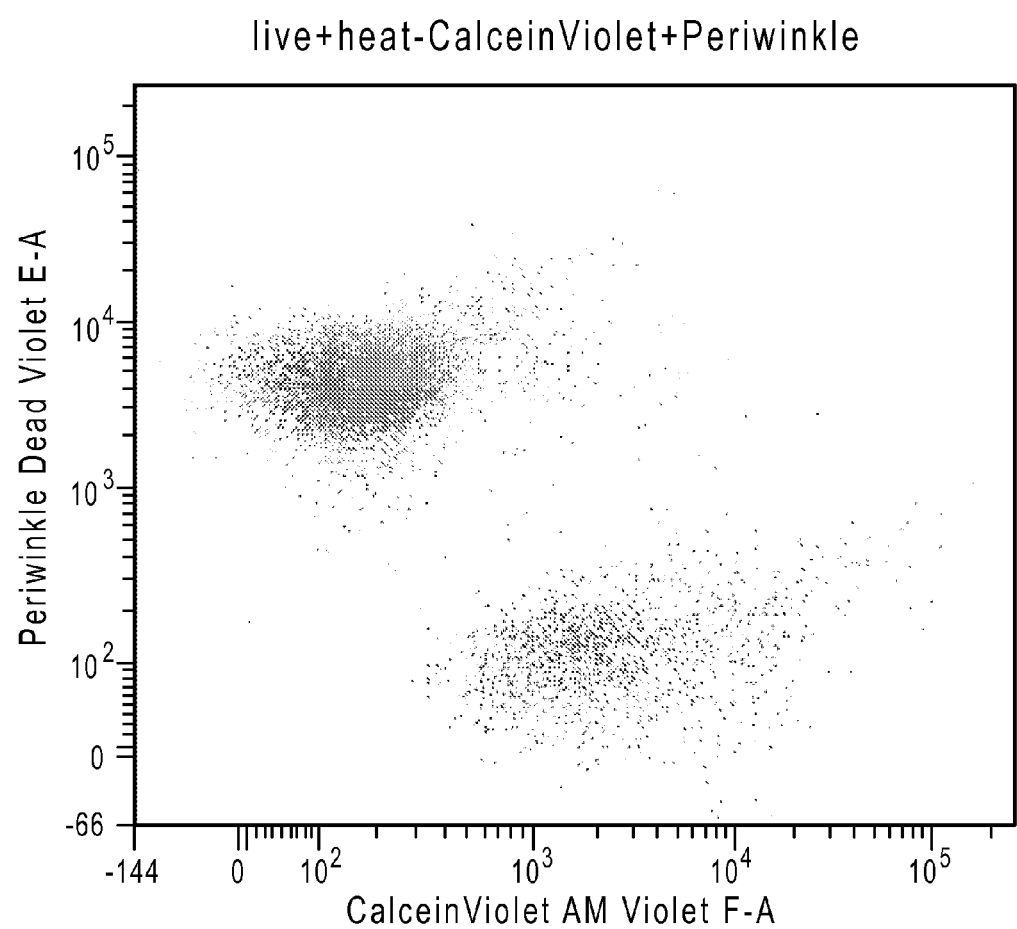
Figure 6D:
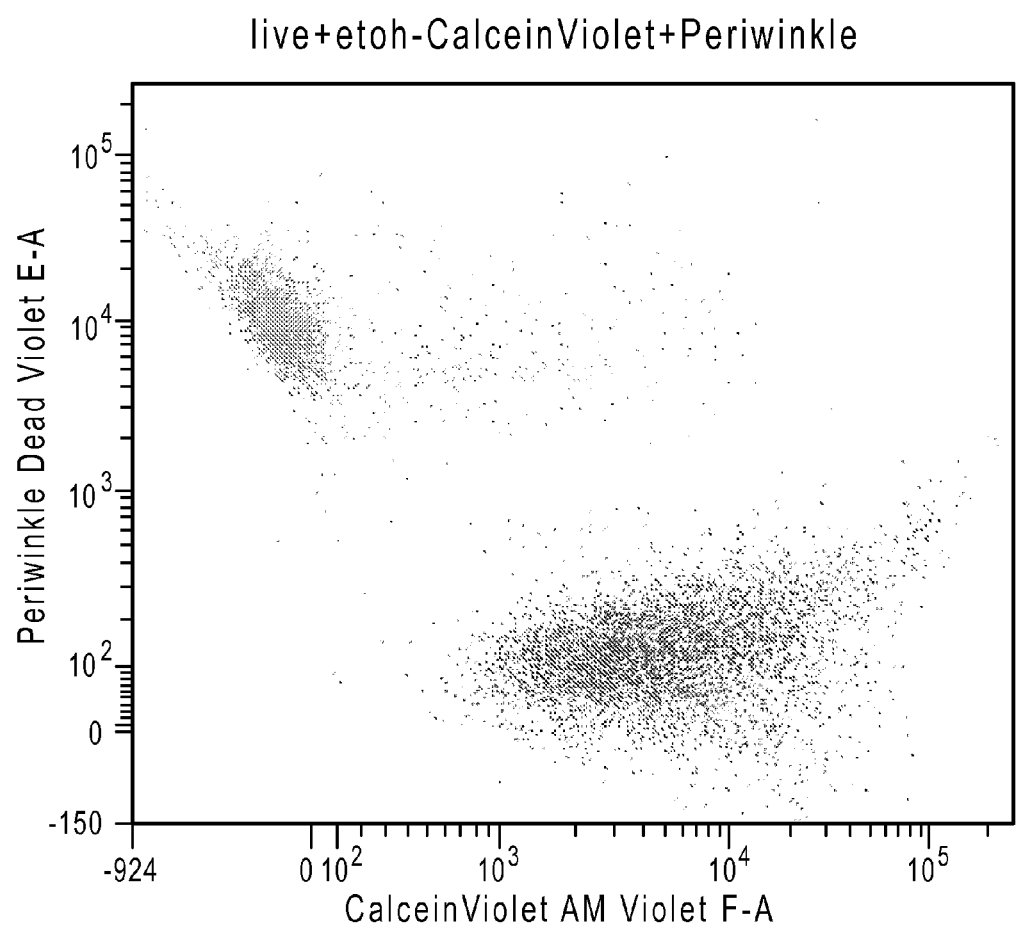

Results: Compound 9A is brighter than Cascade yellow and Compound 9A does not have 488 emission and has very little emission in the Pacific Blue filter off of the violet. See FIG. 3.

Example 36

Comparison of Compound 9A Mouse Anti-Human CD8 to AmCyan Mouse Anti-Human CD8 and CD4

Human PBMC's were harvested from the flow-through fraction of human apheresis. Cells were resuspended at a concentration of 10E6 per ml in PBS containing 2% FBS and 0.1% sodium azide at 4° C. Cells were stained with mouse anti-human CD8 Compound 9A at a concentration of 2 ug/sample or mouse anti-human CD8 AmCyan or mouse anti-human CD4 AmCyan and incubated for 30 minutes. The cells were washed, resuspended and analyzed on a LSRII flow cytometer (BD Bioscience) using a 405 nm violet diode laser (25 mW) and 530/30 or 560/55 nm bandpass filter. The results showed Compound 9A anti-hCD8 was brighter than AmCyan anti-hCD 8 and AmCyan anti-hCD4.

Example 37

Staining of Dead Cells and Fixed Cells with Compound 31

Using four populations of Jurkat cells: live culture cells, aged culture cells, heat-killed cells, and ETOH killed cells, each cell type is suspended at $1 \times 10^6$ cells/ml in PBS. One ml of cell suspension was added to a tube, and 5 μl of a 0.1 mg/ml solution of Compound 31 was added, mixed, and incubated 30 minutes at room temperature protected from light. After incubation, tubes were washed once with PBS, cells were pelleted, and pellet resuspended in one ml PBS. A BD LSRII flow cytometer was used to collect 10,000 events/tube, using 405 nm excitation and 525/50 bandpass. After initial collection, cells were resuspended in 3.7% formaldehyde in PBS, incubated 15 minutes, and re-run on the LSRII.

Live cells were distinguished from dead cells, with the live cells showing fluorescence slightly above autofluorescence and dead cells showing a fluorescence increase of at least one log unit. Using the MFI (Median fluorescent intensity) value of the live cells (MFI=108) and calculating a MFI ratio for each cell type to calculate a Dead:Live ratio, a ratio of 35 was obtained with aged culture cells, a ratio of 92 was obtained with ETON-killed cells, and a ratio of 74 was obtained with heat-killed cells. After fixation, no changes in light scatter or fluorescence were noted. Compound 31 stains positive for dead cells and fixation with 3.7% formaldehyde does not alter results. See, FIG. 5

Example 38

Staining of Dead Cells with Compound 31 and Live Cells with Two Different Calcein AM Stains A mixture of live and heat-killed Jurkat cells and a mixture of live and ethanol-killed Jurkat cells each were suspended at 1×106 cells/ml in PBS. One ml of cell suspension was added to a tube, and 5 μl of a 0.1 mg/ml solution of Compound 31 was added to each set. To one set, calcein green, AM was also added at 50 μM final concentration for dual color staining. To the other set of tubes, calcein violet, AM (Invitrogen Corp. C34858) was added for dual color staining. Tubes were incubated 30 minutes at room temperature protected from light. After incubation, tubes were washed once with PBS, cells were pelleted, and the cell pellet resuspended in one ml PBS. A BD LSRII flow cytometer was used to collect 10,000 events/tube, using 405 nm excitation and 525/50 bandpass for Compound 31, 405 nm excitation with 450/50 bandpass for the calcein violet, AM stain, and 488 nm excitation with 530/30 bandpass for the calcein green, AM stain. Single and dual color fluorescence was collected.

Live cells (as defined by the calcein green, AM and the calcein violet, AM staining) and dead cells (as defined by Compound 31) were easily distinguished as separate and mutually exclusive populations. Compound 31 stains positive for dead cells and negative for live cells. See FIG. 6.

The reagents employed in the examples are commercially available or can be prepared using commercially available instrumentation, methods, or reagents known in the art. The foregoing examples illustrate various aspects of the invention and practice of the methods of the invention. The examples are not intended to provide an exhaustive description of the many different embodiments of the invention. Thus, although the forgoing invention has been described in some detail by way of illustration and example for purposes of clarity of understanding, those of ordinary skill in the art will realize readily that many changes and modifications can be made thereto without departing from the spirit or scope of the appended claims.

We claim:
1. A compound according to the formula:

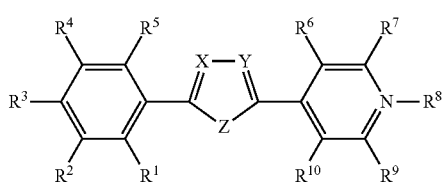

wherein
X is —CR$^{12}$;
Y is —CR$^{12}$;
Z is sulfur;
R$^{12}$ is hydrogen, alkyl, substituted alkyl, alkoxy, hydroxy, sulfo, halogen, amino, substituted amino, aldehyde, carboxylic acid, ester, azido, nitro, nitroso, cyano, or thioether;
R$^1$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^1$ comprises a reactive group, carrier molecule or solid support;
R$^2$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^2$ comprises a reactive group, carrier molecule or solid support;
R$^3$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^3$ comprises a reactive group, carrier molecule or solid support;
R$^4$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^4$ comprises a reactive group, carrier molecule or solid support;
R$^5$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^5$ comprises a reactive group, carrier molecule or solid support;
R$^6$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^6$ comprises a reactive group, carrier molecule or solid support;
R$^7$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^7$ comprises a reactive group, carrier molecule or solid support;
R$^8$ is —(CH$_2$)$_3$SO$_3$—;
R$^9$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^9$ comprises a reactive group, carrier molecule or solid support; and
R$^{10}$ is hydrogen, alkyl, substituted alkyl, alkoxy, hydroxy, sulfo, halogen, amino, substituted amino, aldehyde, carboxylic acid, ester, azido, nitro, nitroso, cyano, thioether, 5-, 6- or 7-aromatic or heteroaromatic ring, substituted 5-, 6- or 7-aromatic or heteroaromatic ring or R$^{10}$ comprises a reactive group, carrier molecule or solid support.

2. The compound according to claim 1, wherein R$^4$ is —SO$_3$—.

3. The compound according to claim 1, wherein R$^3$ is alkoxy.

4. The compound according to claim 1, wherein at least one of R$^1$, R$^2$, R$^3$, R$^4$, R$^5$, R$^6$, R$^7$, R$^8$ or R$^9$ comprises a sulfo group.

5. The compound according to claim 1 wherein at least one of R$^1$, R$^2$, R$^3$, R$^4$, R$^5$, R$^6$, R$^7$, or R$^9$ comprises a reactive group, carrier molecule or solid support.

6. The compound according to claim 1, wherein R$^3$ comprises a reactive group, carrier molecule or solid support.

7. The compound according to claim 1, wherein the reactive group comprises an acrylamide, a carboxylic acid, an activated ester of a carboxylic acid, a succinimidyl ester of a carboxylic acid, a carboxylic ester, an acyl azide, an acyl nitrile, an aldehyde, an alkyl halide, an anhydride, an aniline, an amine, an aryl halide, an azide, an aziridine, a boronate, a diazoalkane, a haloacetamide, a haloalkyl, a halotriazine, a hydrazine, an imido ester, an isocyanate, an isothiocyanate, a maleimide, a phosphoramidite, a reactive platinum complex, a silyl halide, a sulfonyl halide, or a thiol.

8. The compound according to claim 1, wherein the solid support comprises a microfluidic chip, a silicon chip, a microscope slide, a microplate well, silica gels, polymeric membranes, particles, derivatized plastic films, glass beads, cotton, plastic beads, alumina gels, polysaccharides, polyvinylchloride, polypropylene, polyethylene, nylon, latex bead, magnetic bead, paramagnetic bead, superparamagnetic bead, Sepharose, poly(acrylate), polystyrene, poly(acrylamide), polyol, agarose, agar, cellulose, dextran, FICOLL, heparin, glycogen, amylopectin, mannan, inulin, nitrocellulose, diazocellulose and starch.

9. The compound according to claim 1, wherein the carrier molecule comprises an antibody or fragment thereof, an avidin or streptavidin, a biotin, a blood component protein, a dextran, an enzyme, an enzyme inhibitor, a hormone, an IgG binding protein, a fluorescent protein, a growth factor, a lectin, a lipopolysaccharide, a microorganism, a metal binding protein, a metal chelating moiety, a non-biological microparticle, a peptide toxin, a phosphotidylserine-binding protein, a structural protein, a small-molecule drug, a tyramide, an amino acid, a peptide, a protein, a polysaccharide, a nucleotide, a nucleoside, an oligonucleotide, a nucleic acid, a hapten, a psoralen, a drug, a hormone, a lipid, a lipid assembly, a synthetic polymer, a polymeric microparticle, a biological cell or a virus.

10. The compound according to claim 1, that is:

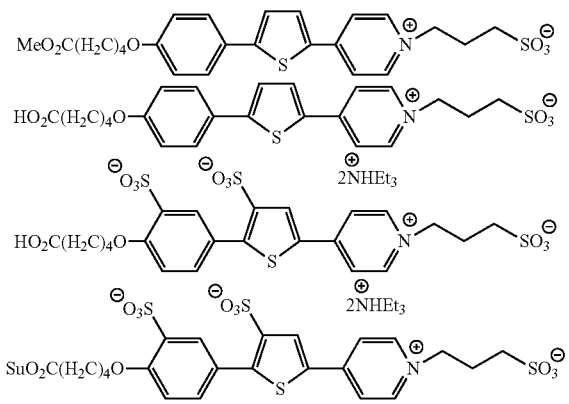

wherein Su is succinimidyl.

11. A method for detecting an analyte in a sample, wherein the method comprises
   a. combining a compound according to claim 1 with a sample to form a combined sample;
   b. incubating the combined sample for a sufficient amount of time for the compound to associate with the analyte in the sample to form an incubated sample;
   c. illuminating the incubated sample with an appropriate wavelength to form an illuminated sample; and
   d. detecting the illuminated sample whereby the analyte in the sample is detected.

12. The method according to claim 11, wherein the illumination and/or detecting step comprises a flow cytometer.

13. A method for forming a dye conjugate, wherein the method comprises:
   a. combining a compound according to claim 1 with a carrier molecule or solid support to form a combined sample; and
   b. incubating the combined sample for a sufficient amount of time for the compound to form a covalent bond with either the carrier molecule or solid support.

14. The method according to claim 13, further comprising separating un-conjugated compound from the compounds that formed a covalent bond with the carrier molecule or solid support.

15. A method for evaluating the viability of cells in a sample, comprising
   a. combining a compound according to claim 1 with a sample to form a combined sample;
   b. incubating the combined sample for a sufficient amount of time for the compound to form a covalent bond with amine groups on a cell membrane of live cells and to form covalent bonds with amine groups inside dead cells in the sample to form an incubated sample;
   c. illuminating the incubated sample with an appropriate wavelength to form an illuminated sample; and
   d. detecting the illuminated sample whereby the via of cells in a sample is evaluated.

16. A kit for detecting an analyte in a sample, wherein the kit comprises:
   a. a compound according to claim 1; and
   b. instructions for detecting the analyte.

\* \* \* \* \*